United States Patent
Wagner et al.

(10) Patent No.: US 10,537,291 B2
(45) Date of Patent: Jan. 21, 2020

(54) MEDICAL PROCEDURE MONITORING SYSTEM

(71) Applicant: VALCO ACQUISITION LLC AS DESIGNEE OF WESLEY HOLDINGS, LTD, Pepper Pike, OH (US)

(72) Inventors: David W. Wagner, Boston, MA (US); Marco Zenati, Belmont, MA (US); J. C. Flaherty, Auburndale, FL (US); R. M. Flaherty, Auburndale, FL (US); Jason Maron, Allston, MA (US)

(73) Assignee: VALCO ACQUISITION LLC AS DESIGNEE OF WESLEY HOLDINGS, LTD, Pepper Pike, OH (US)

( * ) Notice: Subject to any disclaimer, the term of this patent is extended or adjusted under 35 U.S.C. 154(b) by 0 days.

(21) Appl. No.: 15/723,808

(22) Filed: Oct. 3, 2017

(65) Prior Publication Data
US 2018/0153481 A1   Jun. 7, 2018

Related U.S. Application Data

(63) Continuation of application No. 14/414,657, filed as application No. PCT/US2013/050690 on Jul. 16, 2013, now Pat. No. 9,788,799.
(Continued)

(51) Int. Cl.
*A61B 5/00* (2006.01)
*A61B 90/00* (2016.01)
(Continued)

(52) U.S. Cl.
CPC ............ *A61B 5/746* (2013.01); *A61B 5/7278* (2013.01); *A61B 5/7282* (2013.01);
(Continued)

(58) Field of Classification Search
CPC ..... G06F 19/3481; G16H 50/20; G16H 80/00
See application file for complete search history.

(56) References Cited

U.S. PATENT DOCUMENTS 5,623,539 A * 4/1997 Bassenyemukasa .... H04M 1/66
379/114.14
5,675,135 A   10/1997 Friedman et al.
(Continued)

FOREIGN PATENT DOCUMENTS

WO   WO 2008/042119   4/2008

OTHER PUBLICATIONS

Extended European Search Report dated Mar. 8, 2016 for EP application No. 13820457.3.
(Continued)

*Primary Examiner* — Hongmin Fan
(74) *Attorney, Agent, or Firm* — Fay Sharpe LLP

(57) ABSTRACT

A system and method for monitoring a medical procedure performed in a clinical environment is provided. An audio recorder is configured to produce a verbal data signal that is representative of a verbal communication occurring in the clinical environment, and a data analyzer is configured to detect an adverse condition based upon the verbal data signal. An alert module is configured to alert an operator upon the detection of an adverse condition.

253 Claims, 4 Drawing Sheets

Related U.S. Application Data

(60) Provisional application No. 61/671,922, filed on Jul. 16, 2012.

(51) Int. Cl.

| | | |
|---|---|---|
| *A61B 90/50* | (2016.01) | |
| *A61B 34/30* | (2016.01) | |
| *A61B 90/90* | (2016.01) | |
| *G16H 40/20* | (2018.01) | |
| *A61B 17/00* | (2006.01) | |
| *A61C 19/00* | (2006.01) | |

(52) U.S. Cl.
CPC ........ *A61B 17/00234* (2013.01); *A61B 34/30* (2016.02); *A61B 90/361* (2016.02); *A61B 90/50* (2016.02); *A61B 90/90* (2016.02); *A61C 19/00* (2013.01); *G16H 40/20* (2018.01); *A61B 2017/00207* (2013.01); *A61B 2090/502* (2016.02); *H04R 2201/107* (2013.01)

(56) References Cited

U.S. PATENT DOCUMENTS

| | | | |
|---|---|---|---|
| 5,970,457 | A | 10/1999 | Brant |
| 6,231,500 | B1 | 5/2001 | Kehoe |
| 6,406,426 | B1 | 6/2002 | Reuss et al. |
| 6,587,824 | B1 * | 7/2003 | Everhart ................ G10L 15/07 704/243 |
| 6,754,632 | B1 | 6/2004 | Kalinowski et al. |
| 7,203,649 | B1 | 4/2007 | Linebarger et al. |
| 7,258,660 | B1 | 8/2007 | Sarfati |
| 7,752,050 | B1 | 7/2010 | Hameed et al. |
| 7,844,677 | B1 * | 11/2010 | Asher ..................... H04L 43/00 455/428 |
| 8,026,821 | B2 * | 9/2011 | Reeder .................. A61B 5/0002 340/573.1 |
| 8,195,333 | B2 | 6/2012 | Ziegler et al. |
| 8,214,453 | B2 | 7/2012 | Estes |
| 8,223,088 | B1 * | 7/2012 | Gomez ............... G06F 3/03547 345/7 |
| 2003/0110034 | A1 * | 6/2003 | Runge ..................... G10L 17/04 704/246 |
| 2003/0130016 | A1 * | 7/2003 | Matsuura ............... H04R 5/033 455/569.1 |
| 2003/0139778 | A1 * | 7/2003 | Fischell ................ A61B 5/0006 607/3 |
| 2006/0173679 | A1 * | 8/2006 | DelMonego .......... G06F 17/243 704/235 |
| 2007/0136218 | A1 * | 6/2007 | Bauer ................. G06F 19/3481 706/12 |
| 2008/0180213 | A1 * | 7/2008 | Flax ....................... G06F 19/322 340/5.84 |
| 2008/0300572 | A1 * | 12/2008 | Rankers ............. A61B 5/14532 604/504 |
| 2009/0017853 | A1 * | 1/2009 | Ozog .................... H04M 11/022 455/509 |
| 2009/0281809 | A1 | 11/2009 | Reuss |
| 2010/0057646 | A1 * | 3/2010 | Martin .................... G16H 15/00 706/11 |
| 2010/0088108 | A1 * | 4/2010 | Machado ............. G06Q 10/087 705/2 |
| 2010/0142715 | A1 * | 6/2010 | Goldstein ............. G06F 16/686 381/56 |
| 2010/0226306 | A1 * | 9/2010 | Nakashima ........... H04B 7/155 370/315 |
| 2010/0299135 | A1 * | 11/2010 | Fritsch ................ G06F 17/2785 704/9 |
| 2011/0106499 | A1 * | 5/2011 | Huang ................... G01N 29/14 702/184 |
| 2011/0125503 | A1 * | 5/2011 | Dong ...................... G10L 15/22 704/275 |
| 2012/0158432 | A1 | 6/2012 | Jain et al. |
| 2012/0323590 | A1 * | 12/2012 | Udani ................. G06Q 10/103 705/2 |
| 2012/0323597 | A1 | 12/2012 | Woolford |
| 2013/0006625 | A1 * | 1/2013 | Gunatilake ............ G10L 15/26 704/235 |
| 2013/0144629 | A1 * | 6/2013 | Johnston ................ G06F 3/167 704/275 |
| 2013/0151251 | A1 * | 6/2013 | Herz ....................... G10L 15/26 704/235 |
| 2013/0238330 | A1 | 9/2013 | Casella dos Santos |
| 2016/0246929 | A1 * | 8/2016 | Zenati .................... G16H 80/00 |

OTHER PUBLICATIONS

International Search Report and Written Opinion, International Application No. PCT/US2013/050690, dated Mar. 4, 2014, 21 pages.

* cited by examiner

MEDICAL PROCEDURE MONITORING SYSTEM

CROSS REFERENCE TO RELATED APPLICATIONS

This application is a continuation of U.S. patent application Ser. No. 14/414,657, which was filed on Jan. 13, 2015, which is a U.S. National Stage Entry of International Application No. PCT/US2013/050690, which was filed on Jul. 16, 2013, which claims priority to and the benefit of U.S. Provisional Patent Application No. 61/671,922, which was filed on Jul. 16, 2012; the disclosures of all of which are incorporated by reference herein in their entireties.

BACKGROUND OF THE INVENTION

The rate of surgical complications has been estimated to be between 3-17%, worldwide. The Joint Commission, formerly known as the Joint Commission on Accreditation of Healthcare Organizations, identified human factors, communication, and information management to be among the top ten root causes for surgical complications in the past eight years. Data driven decision making is compromised by cognitive overload of surgeons and inability to quickly diffuse information to operating room teams, meaning that high-level patient management and performing attention dedicated technical skills are not always simultaneously exercised. Communication in the operating room is often marred by ambiguity of roles, dysfunctional teams, lack of situational awareness and unfamiliarity with surgeons' stylistic preferences. Studies have shown teamwork/communication disruption causes 52% of interruptions and distractions, and 10% of all communication breakdowns were seen to cause visible delays in surgery.

While checklists have positive effects, there is a need for a truly effective system covering a wide array of system failure modes such as communication breakdown, fatigue, inappropriate staffing, interruptions and inappropriate protocol.

SUMMARY

According to an aspect of the invention, a system for monitoring a medical procedure performed in a clinical environment includes an audio recorder configured to produce a verbal data signal representative of verbal communication that occurs in the clinical environment; a data analyzer configured to receive the verbal data signal from the audio recorder, analyze the verbal data signal and detect at least one adverse condition; and an alert module configured to alert at least one operator when the at least one adverse condition is detected by the data analyzer.

The medical procedure can include a procedure selected from the group consisting of: a surgical procedure such as a minimally invasive surgical procedure, a laparoscopic surgical procedure; an open surgical procedure; an interventional procedure; a reconstructive surgery; a robotic or robotically-enabled procedure; an outpatient procedure; a dental procedure such as a fully anesthetized dental procedure; and combinations of these.

The clinical environment can include a setting selected from the group consisting of: an operating room; a catheterization lab; an intensive care unit; a control room for an operating room; an outpatient surgery treatment room; a dentist's office; a surgeon's office such as a maxillofacial surgeon's office; and combinations of these.

In some embodiments, the audio recorder can include at least one microphone. For example, the audio recorder includes multiple microphones, where a first microphone is positioned in proximity to a first operator and a second microphone in proximity to a second operator. In some embodiments, the audio recorder can include an operator-worn headset. For example, each operator of the at least one operators wears a headset where each headset comprises an identifier associated with the particular operator. In some embodiments, the audio recorder can include an intercom system.

The audio recorder can be configured to produce a non-verbal data signal. The non-verbal data signal can include an audio signal produced by equipment positioned in the clinical environment such that the data analyzer can receive the non-verbal data signal from the audio recorder, analyze the non-verbal data signal and detect an equipment status signal. In an example, the equipment status signal includes an equipment warning signal.

The system can include a video camera configured to produce a video data signal. The data analyzer can receive and analyze the video data signal from the video camera. The data analyzer can detect an operator gesture, for example a gesture selected from the group consisting of: a head nod or other affirmatory response; a head shake or other non-affirmatory response; a shrug; an indecisive response; and combinations of these. The data analyzer can detect at least one spoken word in the video data signal. The data analyzer can detect at least one adverse condition in the video data signal. The data analyzer can combine the verbal data signal and the video data signal to produce a combined signal so as to analyze the combined signal. From an analysis of the combined signal, the data analyzer can detect an adverse condition.

The verbal data signal can include communication data received from a single operator. The verbal data signal can include communication data received from multiple operators, for example communication data from at least a first operator and a second operator where the data analyzer is configured to differentiate the communication data of the first operator from communication data from the second operator. The verbal data signal can include verbal communication that occurred prior to, during and/or after the performance of the medical procedure.

The data analyzer can include a component selected from the group consisting of: microprocessor; microcontroller; analog to digital converter; digital to analog converter; and combinations of these.

The data analyzer can include spoken word recognition software employing at least one algorithm where the algorithm converts the verbal data signal to text data. The at least one algorithm can be biased to correlate at least a portion of the verbal data signal to one or more medical terms, for example where the system includes a library of medical terms. The at least one algorithm can be biased to correlate at least a portion of the verbal data signal to one or more terms input by an operator. The at least one algorithm can be biased to correlate at least a portion of the verbal data signal to at least one quantitative value input by an operator. In some embodiments, the at least one quantitative value can include a range of values. The at least one algorithm can be biased to correlate at least a portion of the verbal data signal to a range of quantitative values wherein the range comprises quantitative values that are typically associated with a parameter. The at least one algorithm can be biased to correlate at least a portion of the verbal data signal to a previously received verbal data signal. In some embodiments, the at least a portion of the verbal data signal comprises a quantitative value.

The data analyzer can include a memory module configured to store patient historic data. Patient historic data can include data selected from the group consisting of: sex, age, height, weight, race, medical history; and combinations of these. In some embodiments, the data analyzer can employ an algorithm to extract the patient historic data from the verbal data signal. Patient historic data can be entered into an input device, for example an operator can enter the patient historic data into a device selected from the group consisting of: a keyboard; a touch screen display; and combinations of these.

The data analyzer can be configured to identify patient data in the verbal data signal. Examples of patient data include: ACT; blood pressure; heart rate; pulse rate; respiratory rate; glucose levels; saturated $O_2$ pressure; saturated $CO_2$ pressure; core body temperature; skin temperature; total lung capacity; residual volume; expiratory reserve volume; vital capacity; tidal volume; alveolar gas volume; actual lung volume; EEG bands such as Delta, Theta, Alpha, Beta, Gamma and Mu; EKG information such as RR interval, P wave length/amplitude, PR interval, amplitude of QRS complex, J-point detection, absolute and relative refractory periods, QT interval and U & J Wave detection; blood volume; extra embolic gases; heparin volume; protamine sulfate volume; and combinations of these.

The data analyzer can be configured to identify equipment data in the verbal data signal. Examples of equipment data include: instructions to turn a piece of equipment on or off; instructions to modify the settings of one or more pieces of equipment; and combinations of these.

The data analyzer can be configured to identify procedure data in the verbal data signal. Examples of procedure data include: total procedure length; length of a procedural step; time of initiation of a procedural step; time since last administration of a drug or other agent; and combinations of these. Examples of a procedural step include: procedural steps selected from the group consisting of: patient preparation; anesthesia induction; opening/sternotomy; initiation of bypass; cardiac repair; termination of bypass; closure; post-op; anesthesia; insufflation; laparoscopic insertion such as laparoscopic insertion prior to a cholecystectomy; diagnosis confirmation; port incisions; removing bile; grasping a structure such as a gallbladder; isolating and dividing structures; separation of a first structure from a second structure such as a gallbladder from a liver; removal of a structure such as a gallbladder; irrigation such as abdominal wall irrigation; prostatectomy such as a robotic prostatectomy; docking of a robot; dissection such as SV dissection; hemostasis; completion of anastamosis; removal of drapes; and combinations of these.

The data analyzer can be configured to identify a request for information data in the verbal data signal. Examples of information data include: a patient parameter; a procedural parameter; an equipment parameter; and combinations of these. A quantitative and/or qualitative response to the request can be provided.

The data analyzer can be configured to identify an acknowledgement of receipt of information, for example where the system includes a library of acknowledgement terms.

The data analyzer can be configured to correlate the received verbal data signal to a first operator or to a second operator. In some embodiments, the data analyzer can include an algorithm for detecting the adverse condition where the algorithm comprises a first analysis on data correlated to the first operator and a second, different analysis on data correlated to the second operator. In some embodiments, the data analyzer can correlate the verbal data signal of the first operator based on a first identifier and correlate the verbal data signal of the second operator based on a second identifier, where the first identifier is different from the second identifier, for example where a headset worn by each operator includes the identifier.

The data analyzer can be configured to correlate the verbal data signal to an operator type. Examples of operator types include: a surgeon; an anesthesiologist; a scrub nurse; a circulating nurse; hospital administrator; and combinations of these. In some embodiments, the data analyzer can include an algorithm, where the algorithm detects the adverse condition based on the operator type and the verbal data signal.

The data analyzer can be configured to filter and/or segregate verbal data received from at least one operator. In some embodiments, the filtered and/or segregated verbal data is prioritized based on an operator hierarchy. Additionally, the data analyzer can be configured to filter and/or segregate verbal data received from a non-operator.

The data analyzer can include a memory module. One or more portions of the verbal and/or video data signal can be stored in the memory module. One or more portions of a processed verbal and/or video data signal can be stored in the memory module. A library of values can be stored in the memory module, for example a library of multiple spoken word terms to be recognized and/or a library of one or more quantitative values where the data analyzer includes an algorithm that compares the verbal data signal to the one or more quantitative values. Historic medical statistics and/or other medical data can be stored in the memory module.

The data analyzer can detect the at least one adverse condition based on data extracted from the verbal data signal exceeding a threshold, for example where the threshold includes a value or a range of values. The value or range of values can be inputted to the system by one or more operators and can relate to at least one of a patient, procedural or equipment parameter. Additionally, the data analyzer can detect the at least one adverse condition based on: an identification of a key word in the verbal data signal; a detection of an unrecognized voice in the verbal data signal; a detection of an unrecognized term in the verbal data signal; a determination that a first operator has been active and/or present above a threshold of time such as when the first operator is a surgeon; a detection of a heightened frequency of recognized terms at an improper time; a lack of receipt of information; a determination that multiple pieces of similar data have not been received within a pre-determined time interval such as an operator adjustable time interval; a determination that a particular operator is not present; an analysis of patient historic data; an analysis of a set of medical statistics such as a set of medical statistics that are pre-selected by an operator; and combinations of these.

In some embodiments, the alert module can be configured to notify a single operator of the detection of an adverse condition. The notification can be based on an identifier associated with that particular operator, for example via a headset worn that by that operator. In some embodiments, the alert module can be configured to notify multiple operators of the detection of an adverse condition.

The alert module can include an audio transducer configured to produce an audible beep when an adverse condition has been detected. In some embodiments, the audio transducer can be configured to produce a first audio pattern when a first adverse condition is detected and a second audio pattern when a second adverse condition is detected. The sounds and audio patterns can include a computer generated voice; a recording of a human voice; and combinations of these.

In some embodiments, the alert module can include a visual display. For example, the visual display can provide alpha-numeric text when an adverse condition is detected. In some embodiments, the alert module can include a tactile transducer, for example an operator-worn tactile transducer that can vibrate upon the detection of an adverse condition. In some embodiments, the alert module can include multiple alert transducers, for example an audio transducer such as speaker and a piezo transducer; a visual transducer such as an LCD screen, a touch screen, and a light such as an LED; a tactile transducer such as a vibrating transducer and a thermal transducer; and combinations of these.

The system can include a data input module configured to allow at least one operator to input data to the system. The data input module can include a voice data input module such as a microphone and/or the input module can include a text data input module such as a keyboard; a touch screen; a motion-sensing input device; a cell phone; a handheld electronic organizer; a mouse; a tablet; a hospital computer or computer network; a wireless connection such as a cellular service; an internet connection; an electronic file transfer port such as USB port; a memory storage device such as a USB memory stick; and combinations of these.

Operator voice data can be entered into the input module from any or all operators so that the data analyzer can convert the verbal data signal to text data based on the operator voice data. Additionally, the data analyzer can correlate the verbal data signal to the operator voice data to identify the operator. In some embodiments, the data analyzer includes memory, where the operator input data includes spoken word terms, and where the data analyzer can store the spoken word terms in the memory. Then, an algorithm can compare the verbal data signal to the spoken word terms stored in the memory which converts the verbal data signal to text data. In some embodiments, the data analyzer includes memory, where the operator input data comprises quantitative data, and where the data analyzer can store the quantitative data in the memory. Then, an algorithm can compare the verbal data signal to quantitative data stored in the memory, for example where the quantitative data includes a threshold value.

The data input module can communicate with a healthcare information system, for example to send and/or receive patient, procedural or other medical information from the healthcare information system.

The system can include a data output module configured to provide patient and/or procedural information to at least one operator. The patient and/or procedural information can be provided in response to a request by the at least one operator. Examples of patient and/or procedural information includes: a current or real-time parameter; a historic parameter; an average of multiple parameter values; a maximum of multiple parameter values; and combinations of these. Other examples of information that can be provided by the data output module includes: an adverse condition detected; an operator's entry and/or exit time into the clinical setting; a procedure event that surpasses a threshold; an evidence-based decision support reminder; a captured video; a recommendation generated by the data analyzer; and combinations of these. The information can be provided in paper and/or electronic form, in real-time and/or after the completion of a procedure.

The data output module can communicate with a healthcare information system, for example to send and/or receive patient, procedural or other medical information from the healthcare information system.

The system can include a data monitoring module. In some embodiments, the data monitoring module can confirm that the proper information is received, for example to confirm that proper information is continually received within a pre-determined time interval.

The system can include an operator position monitoring module. In some embodiments, the operator position monitoring module can monitor an operator position by detecting an operator voice in the verbal data signal. The operator position monitoring module can include a motion sensor; a video camera; a timecard entry assembly; and combinations of these.

The system can include at least one sensor. Examples of sensors include: a temperature sensor; an acoustic sensor; an electromagnetic sensor; a pressure sensor; a motion sensor; and combinations of these.

The system can include a patient treatment device. Examples of a patient treatment device include: scalpel; electrocautery device; grasper; guidewire; interventional catheter; anesthesia injection device; RF or cryogenic ablation equipment; retractor; ECMO device; ventricular assist device; ventilator; bone awl; bone tamper; bone gouge; bone file; bone mallet; osteotome; defibrillator; drill; radiosurgery system; CPB machine; endoscope; cross clamp; robotic surgical system; colonoscope; polytectomy snare; and combinations of these. In some embodiments, the treatment device can be modified upon the detection of an adverse event, for example the treatment device can be powered down or otherwise disabled.

The system can include a checklist. At least a portion of the checklist can be customized for a particular operator, for example prior to the performance of a medical procedure. In some embodiments, the data analyzer can detect an adverse condition based upon an analysis of the checklist.

According to another aspect of the invention, a method for monitoring a medical procedure performed in a clinical environment includes producing a verbal data signal representative of verbal communication that occurs in the clinical environment; receiving the verbal data signal; analyzing the verbal data signal; detecting at least one adverse condition; and alerting at least one operator when the at least one adverse condition is detected.

The method can further comprise producing a non-verbal data signal and/or a video data signal. These signals can then be received and analyzed by a data analyzer.

Receiving the verbal data signals can include receiving communication data from a single operator. Receiving the verbal data signals can include receiving communication data from multiple operators such as a first and a second operator wherein the method further comprises differentiating the communication data of the first operator from the communication data of the second operator. Receiving the verbal data signals can include receiving communication data occurring prior to, during, and/or after the performance of a medical procedure.

Analyzing the verbal data signal can include: converting the verbal data signal to text data via spoken word recognition software employing at least one algorithm for example where the algorithm correlates at least a portion of the verbal data signal to one or more medical terms stored in a library; correlating at least a portion of the verbal data signal to one or more terms input by an operator; correlating at least a portion of the verbal data signal to at least one quantitative value or range of quantitative values input by an operator; correlating at least a portion of the verbal data signal to a range of quantitative values wherein the range comprises quantitative values that are typically associated with a parameter; correlating at least a portion of the verbal data signal to a previously received verbal data signal such as where the verbal data signal includes a quantitative value; and combinations of these.

The method can further comprise storing patient historic data. Examples of patient historic data includes: sex; age; height; weight; race; medical history; and combinations of these. The method can further comprise extracting the patient historic data from the verbal data signal. The method can further comprise entering the patient historic data via an input device such as a keyboard; a touch screen display; and combinations of these.

The method can further include identifying patient data in the verbal data signal. Examples of patient data includes: ACT; blood pressure; heart rate; pulse rate; respiratory rate; glucose levels; saturated $O_2$ pressure; saturated $CO_2$ pressure; core body temperature; skin temperature; total lung capacity; residual volume; expiratory reserve volume; vital capacity; tidal volume; alveolar gas volume; actual lung volume; EEG bands such as Delta, Theta, Alpha, Beta, Gamma and Mu; EKG information such as RR interval, P wave length/amplitude, PR interval, amplitude of QRS complex, J-point detection, absolute and relative refractory periods, QT interval and U & J Wave detection; blood volume; extra embolic gases; heparin volume; protamine sulfate volume; and combinations of these.

The method can further include identifying equipment data in the verbal data signal. Examples of equipment data include: instructions to turn a piece of equipment on or off; instructions to modify the settings of one or more pieces of equipment; and combinations of these.

The method can further include identifying procedure data in the verbal data signal. Examples of procedure data include: total procedure length; length of a procedural step; time of initiation of a procedural step; time since last administration of a drug or other agent; and combinations of these. Examples of procedural steps include: patient preparation; anesthesia induction; opening/sternotomy; initiation of bypass; cardiac repair; termination of bypass; closure; post-op; anesthesia; insufflation; laparoscopic insertion such as laparoscopic insertion prior to a cholecystectomy; diagnosis confirmation; port incisions; removing bile; grasping a structure such as a gallbladder; isolating and dividing structures; separation of a first structure from a second structure such as a gallbladder from a liver; removal of a structure such as a gallbladder; irrigation such as abdominal wall irrigation; prostatectomy such as a robotic prostatectomy; docking of a robot; dissection such as SV dissection; hemostasis; completion of anastamosis; removal of drapes; and combinations of these.

The method can further include identifying a request for information data in the verbal data signal, for example a request for information selected from the group consisting of: a patient parameter; a procedural parameter; an equipment parameter; and combinations of these. The method can further include providing a quantitative and/or qualitative response to the request.

The method can further include identifying an acknowledgement of receipt of information wherein the identification of the acknowledgement is based on a library of acknowledgement terms.

The method can further include correlating the verbal data signal to a first operator or to a second operator. In some embodiments, an adverse condition can be detected via an algorithm via an algorithm, where the algorithm comprises a first analysis on data correlated to a first operator and a second, different analysis on data correlated to a second operator. The method can further include correlating the verbal data signal of the first operator based on a first identifier and correlating the verbal data signal of the second operator based on a second identifier, wherein the first identifier is different from the second identifier.

The method can further include correlating the verbal data signal to an operator type, for example where an adverse condition is detected based on the operator type and the verbal data signal via an algorithm.

The method can further include filtering and/or segregating verbal data received from at least one operator and/or non-operator. In some embodiments, the method further includes prioritizing the filtered and/or segregated verbal data based on an operator hierarchy.

The method can further comprise storing data selected from the group consisting of: one or more portions of the verbal data signal; one or more processed data signals; a library of values where the values include spoken words to be recognized and/or quantitative values; historic medical statistics and/or other medical data; one or more portions of a video data signal produced by a video camera; and combinations of these.

Detecting the adverse condition can be based on: data extracted from the verbal data signal exceeding a threshold; an identification of a key word in the verbal data signal; a detection of an unrecognized voice in the verbal data signal; a detection of an unrecognized term in the verbal data signal; a determination that a first operator has been active and/or present above a threshold of time; a heightened frequency of recognized terms at an improper time; a lack of receipt of information; a determination that multiple pieces of similar data have not been received within a pre-determined time interval; a determination that a particular operator is not present; an analysis of patient historic data; an analysis of a set of medical statistics; and combinations of these.

Alerting the at least one operator when the adverse condition is detected can include alerting a single operator or multiple operators. Alerting the at least one operator when the adverse condition is detected can include producing at least one of an audible sound; a tactile feedback; or a visual display.

The method can further include entering data into a data input module, for example voice data and/or text data. Entering data can include receiving operator voice data from a first operator via the input data module. The method can further include converting the verbal data signal to text data based on the received first operator voice data, correlating the verbal data signal to the operator voice data to identify the first operator, and storing the operator voice data in a memory. Additionally, quantitative data can be stored in memory, for example to compare the verbal data signal to the quantitative data where the quantitative data includes a threshold value.

The method can further include transmitting information from a healthcare information system to the data input module.

The method can further include providing patient and/or procedural information to at least one operator via an output module, for example where the patient and/or procedural information is provided in response to a request by the operator. Examples of patient and/or procedural information include: a current or real-time parameter; a historic parameter; an average of multiple parameter values; a maximum of multiple parameter values; and combinations of these. The information can be provided in paper and/or electronic form, in real-time and/or after a procedure. The method can further include transferring the information to and/or from a healthcare information system.

The method can further include confirming proper information is received via a data monitoring module, for example confirming the proper information is continually received within a pre-determined time interval.

The method can further include monitoring an operator position by detecting an operator voice in the verbal data signal via an operator position monitoring module, for example where the operator position is monitored via at least one of a motion sensor; a video camera; or a timecard entry assembly.

The method can further include sensing at least one parameter via at least one sensor. Examples of a sensor include: a temperature sensor; an acoustic sensor; an electromagnetic sensor; a pressure sensor; a motion sensor; and combinations of these.

The method can further include treating a patient via a patient treatment device. Examples of a treatment device can include scalpel; electrocautery device; grasper; guidewire; interventional catheter; anesthesia injection device; RF or cryogenic ablation equipment; retractor; ECMO device; ventricular assist device; ventilator; bone awl; bone tamper; bone gouge; bone file; bone mallet; osteotome; defibrillator; drill; radiosurgery system; CPB machine; endoscope; cross clamp; robotic surgical system; colonoscope; polytectomy snare; and combinations of these. The method can further include modifying the treatment device if an adverse event is detected, for example disabling or powering down the treatment device.

The method can further include analyzing a checklist and detecting the at least one adverse condition based upon the analysis of the checklist. The method can include customizing the checklist so that at least a portion of the checklist is customized for a particular operator, for example where the checklist is customized prior to the performance of a medical procedure.

The method can be performed using the system described herein.

The technology described herein, along with the attributes and attendant advantages thereof, will best be appreciated and understood in view of the following detailed description taken in conjunction with the accompanying drawings in which representative embodiments are described by way of example.

DETAILED DESCRIPTION OF THE DRAWINGS

Reference will now be made in detail to the present embodiments of the technology, examples of which are illustrated in the accompanying drawings. The same reference numbers are used throughout the drawings to refer to the same or like parts.

The systems, devices and methods disclosed herein are configured to detect and analyze a wide array of adverse events occurring during a medical procedure such as communication breakdown, fatigue, inappropriate staffing, interruptions and inappropriate protocol. Further, the medical team can be alerted of such adverse events, thus improving the outcome for both the patient and the medical team.

The term "operator" shall refer to one or more individuals, singly or in combination, who provide input data and/or receive output data from the system of the present inventive concepts. Operators can include but are not limited to: surgeons; surgeons' assistants; nurses; health care providers; insurance providers; patients; and combinations of these.

Figure 1:
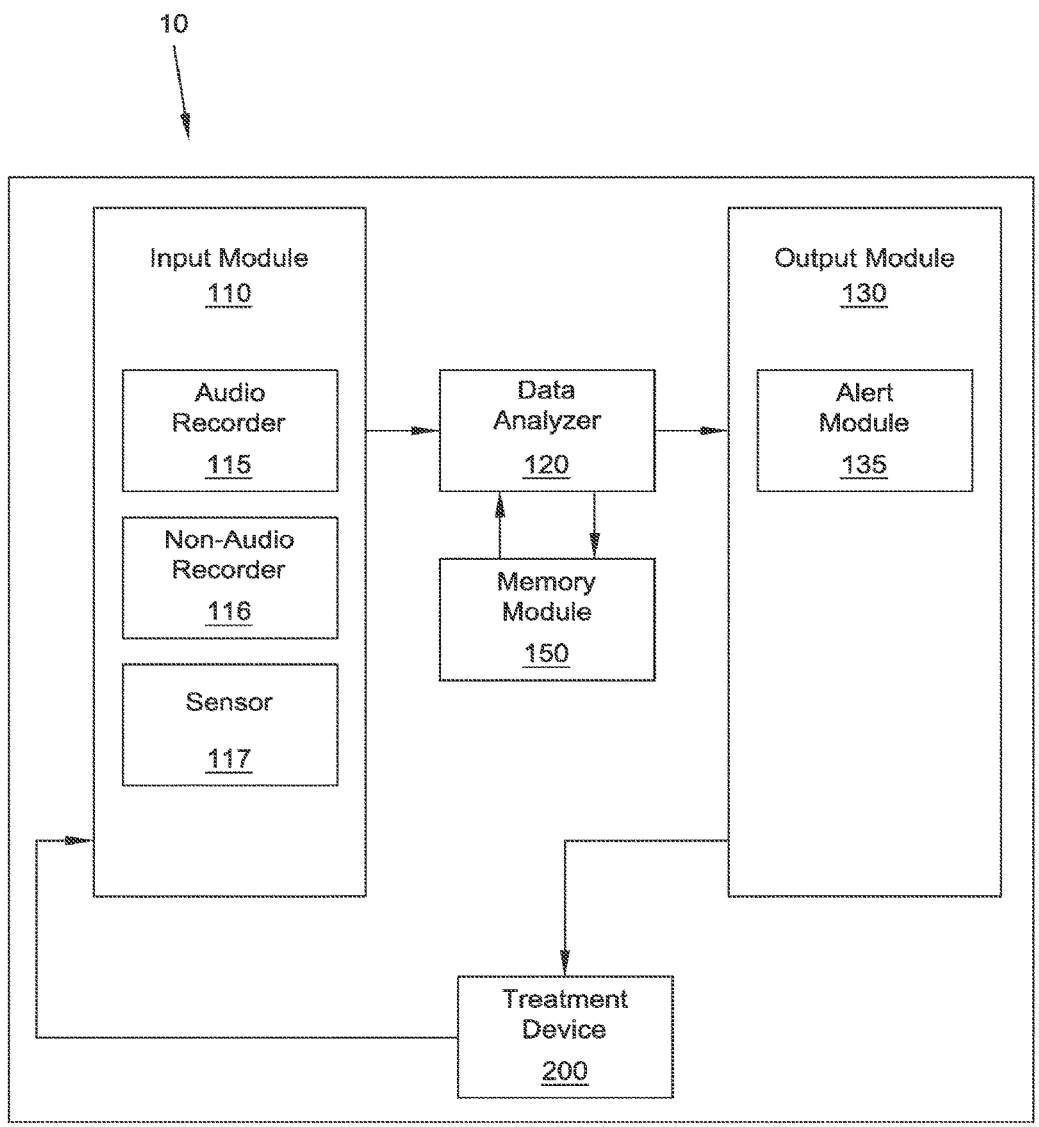
FIG. 1 illustrates a system for monitoring a medical procedure performed in a clinical environment, consistent with the present inventive concepts.

FIG. 1 illustrates a system for monitoring a medical procedure performed in a clinical environment, consistent with the present inventive concepts. System 10 includes input module 110, data analyzer 120 and output module 130. Input module 110 includes audio recorder 115, configured to produce a verbal data signal representative of one or more verbal communications that occur in the clinical environment. Input module 110 can further include non-audio recorder 116, configured to produce a non-verbal data signal representative of one or more non-verbal communications that occur in the clinical environment. Data analyzer 120 is configured to receive the verbal data signal from input module 110 and at least detect one or more adverse conditions that have occurred in the clinical environment. Output module 130 is configured to provide information to one or more operators of system 10. Output module 130 can include alert module 135, configured to provide an audio or other alert notifying one or more operators of system 10 that an adverse condition has been detected by data analyzer 120.

System 10 may be utilized during various types of medical procedures. For example, system 10 may be used during a surgical procedure, such as a minimally invasive surgical procedure, a laparoscopic surgical procedure and an open surgical procedure. Alternatively or additionally, system 10 may be used during an interventional medical procedure. Applicable medical procedures can include but are not limited to: reconstructive surgery; concomitant surgery; a robotic or robotically-enabled procedure; an outpatient procedure; a dental procedure such as a fully anesthetized dental procedure; and combinations of these.

System 10 may be used in various clinical environments, such as a clinical setting selected from the group consisting of: an operating room; a catheterization lab; an intensive care unit; a control room for an operating room; an outpatient surgery treatment room; a dentist's office; a surgeon's office such as a maxillofacial surgeon's office; and combinations of these.

System 10 may be configured to interface with one or more operators. An operator can be any member of the hospital staff, for example a surgeon; an anesthesiologist; a scrub nurse; a circulating nurse; and a hospital administrator. In some embodiments, the patient is an operator of the system such as when a spoken word of the patient is recorded by audio recorder 115 and/or another component of input module 110 and analyzed from data analyzer 120.

In some embodiments, an operator, for example a primary user such as a surgeon, can enter data into input module 110, such as via audio recorder 115 and/or non-audio recorder 116, at any time prior to, during and/or subsequent to a medical procedure performed on a patient. Audio recorder 115 can include one or more audio recording devices selected from the group consisting of: a microphone; an operator-worn microphone or headset (wireless or with cable); a room microphone; an omnidirectional microphone; a Bluetooth device; a wireless device; a telephone; a mobile telephone; and combinations of these. Non-audio recorder 116 can include one or more devices selected from the group consisting of: a keyboard; a touch screen; a motion-sensing input device; a mouse; a tablet; a cell phone; a handheld electronic organizer; a hospital computer or computer network; a wireless connection such as a cellular service; an internet connection; an electronic file transfer port such as USB port; a memory storage device such as a USB memory stick; and combinations of these. An application can be stored in one or more modules of system 10 enabling an operator to select a particular type and/or form of information to be communicated by system 10 to one or more operators. In some embodiments, an operator selects one or more patient and/or procedural parameters to be communicated and recorded by system 10, such as a communication made by an operator and/or produced by output module 130. Additionally, an operator can customize which particular operator should report the information and how frequently it should be reported by an operator and/or output module 130. Further, the customization can include to whom the information should be reported. For example, an operator can identify a particular operator that should report (e.g. verbally state) the patient's blood pressure. In some embodiments, the frequency of reporting can be included, such as reporting needing to occur at least every five minutes. In some embodiments, an operator can identify a particular adverse condition that should be monitored for by data analyzer 120. In some embodiments, an operator can enter quantitative data into input module 110, such as a quantitative value for a threshold, where data analyzer 120 includes an algorithm configured to compare the threshold to a verbal data signal. In some embodiments an operator can enter a library of keywords associated with a parameter, such as a patient and/or procedural parameter that may be requested during a medical procedure (e.g. "blood pressure", "ACT level", "EKG status", and the like) Input module 110 may be configured to receive a library of keywords associated with one or more particular adverse conditions, and data analyzer 120 configured to identify these keywords. Non-limiting examples of non-technical keywords include: "help"; "code"; "tanking"; "slipping"; "falling"; "burning"; "lethal"; "fatal"; "overdose"; "pale"; "hot"; "cold"; "unstable". Non-limiting examples of technical keywords include: "hyperthermic"; "hypothermic"; "hypoxic"; "hyperoxic"; "hypocapnic"; "hypercapnic"; "asystole"; "tachycardia"; "bradycardia"; "fibrillating"; "a-fib"; "v-fib"; "hypoglycemic"; "hyperglycemic"; "long-QT"; and combinations of these.

In some embodiments, system 10 can be configured such that audio recorder 115 receives voice data, e.g. at least one spoken word, from each operator of system 10. This voice data can be used by data analyzer 120 to identify a particular operator's voice based on the stored word or words.

System 10 can be configured to allow an operator to import, record or otherwise enter various forms of data via input module 110, such as via non-audio recorder 116. Data may include non-patient data, hereinafter "external data", which can include medical treatises, medical statistics, or any other medical information that is publicly or privately available. External data to be included can be selected and/or filtered by an operator of system 10. For example, an operator can enter and/or filter external information that is particularly relevant to the procedure to be performed or relevant to the particular patient's medical history and/or the patient's current medical status. Alternatively, entire treatises, books, or other medical sources can be entered into system 10 via input module 110.

System 10 can be configured to allow an operator to import, record or otherwise enter patient data via input module 110, such as patient data collected prior to the medical procedure being performed. Patient data can include but is not limited to: sex; age; height; weight; race; medical history; and combinations of these.

Data entered into input module 110 can be entered prior to, during and/or subsequent to a medical procedure such as surgery. The data entered can be updated, deleted, or otherwise modified at any time prior to, during and/or subsequent to the procedure by one or more of the operators, such as by an authorized or otherwise pre-determined operator. In some embodiments, system 10 may be configured to permit a limited number or subset of operators to enter, update, delete, or otherwise modify one or more sets of data entered into and/or contained within system 10.

In some embodiments, system 10 can communicate with a healthcare information system, for example input module 110 can receive information from the healthcare information system such as information relevant to the particular patient and/or procedure to be performed, for example patient or non-patient clinical, historic data. Such information includes but is not limited to: pre-operative risk calculations for surgical morbidities; intraoperative risk calculations for surgical morbidities; success rate of sub-procedures given health record; and combinations of these.

System 10 includes audio recorder 115 configured to record a verbal communication and produce a verbal data signal that is representative of the verbal communication. The verbal communication can be a communication occurring prior to, during, and/or subsequent to a medical procedure. For example, a verbal communication occurring prior to a procedure can include input data being entered into input module 110 via audio recorder 115. A verbal communication occurring during a procedure can include but is not limited to: a notification of a patient, procedural and/or equipment parameter; a request for data; an acknowledgment of received data; and combinations of these.

Audio recorder 115 can include at least one microphone, and in some cases, audio recorder 115 includes multiple microphones. In some embodiments, a microphone can be in proximity to each operator, for example, a first microphone can be positioned in proximity to a first operator, and a second microphone can be positioned in proximity to a second operator.

In some embodiments, audio recorder 115 includes a headset worn by each operator. The system can receive and/or transmit audio to each operator wearing a headset, or the system can receive and/or transmit audio to a particular operator. In some embodiments, each headset comprises a unique identifier associated with each operator such that data analyzer 120 can correlate a verbal data signal to a specific operator, for example an identifier such as a SIM card. Alternatively or additionally, audio recorder 115 can include an intercom system such that all operators can receive and/or transmit audio simultaneously. In some embodiments, audio recorder 115 can be configured such that only a particular operator's verbal communications is transmitted to the remaining operators present in the clinical environment while the remaining operators are muted, for example in a case where the particular operator is the lead surgeon and he or she desires to communicate data to all other operators present in the clinical environment.

Alternatively or additionally, audio recorder 115 and/or non-audio recorder 116 can include a video camera configured to produce a video data signal. The video camera can detect an operator gesture, for example a gesture including but not limited to a head nod or other affirmatory response; a head shake or other non-affirmatory response; a shrug; an indecisive response; and combinations of these. The video camera can also detect the speech of an operator. The gestures and/or speech are converted to a video data signal such that the video data signal can be analyzed by data analyzer 120, such as to detect an adverse condition. In some embodiments, input module 110 comprises a video camera and at least one microphone such that data analyzer 120 combines a verbal data signal with the video data signal and analyzes the combined signal. In cases where the verbal data is not heard, data analyzer 120 can analyze the video data signal to detect an adverse condition. Conversely, if the video data is not seen, data analyzer 120 can analyze the verbal data signal to detect an adverse event.

A verbal data signal can be representative of a verbal communication received from a single operator and/or multiple operators. In the case of multiple operators, system 10 is configured to differentiate verbal data signals from a first operator and verbal data signals from a second operator. The verbal data signal can be representative of verbal communication occurring prior to, during, and/or after the medial procedure.

In some embodiments, system 10 is configured to produce non-verbal data signals. In some embodiments, the non-verbal data signal can include an audio signal produced by a piece of equipment located in the clinical environment in the form of an equipment status signal. For example, if a piece of equipment requires maintenance, an operator can be alerted to the condition via an equipment warning signal.

System 10 can further comprise a memory storage device, memory module 150, which is configured to store data, such as data entered into input module 110 and/or produced by data analyzer 120. In some embodiments, at least a portion of the verbal data signals and/or video data signals that are received and/or processed (i.e. analyzed by data analyzer 120) as well as the verbal communications and gestures captured by audio recorder 115, can be stored in the memory module. System 10 can include a method of replaying audio, video and/or other recordings, such as via output module 130.

System 10 includes data analyzer 120 configured to receive a verbal data signal from audio recorder 110, analyze the verbal data signal, and detect at least one adverse condition. Data analyzer 120 includes various electronic and other componentry, such as componentry selected from the group consisting of: microprocessor; microcontroller; analog to digital converter; digital to analog converter; and combinations of these. Data analyzer 120 can include spoken word recognition software employing at least one algorithm that converts the verbal data signal to text data. In some embodiments, the algorithm can be biased to correlate at least a portion of the verbal data signal to one or more medical terms. System 10 can further comprise a library of medical terms, such as a library of medical terms stored in memory module 150 where the algorithm's bias is based on the library of medical terms. The library of medical terms can be imported via input module 110, such as data input to system 10 by an operator and/or an external data source. The external data source can include medical treatises, medical statistics, or any other medical information that is publicly or privately available.

Data analyzer 120 can include an algorithm configured to extract the patient historic data stored in the memory module from the verbal data signal. In some embodiments, data analyzer 120 can include an algorithm that is biased to correlate at least a portion of the verbal data signal to at least one quantitative value input by a primary user. The algorithm can be biased to a range of values. In one example, the range of values can include values that are typically associated with a particular parameter, so for instance, if a blood pressure reading typically ranges within 100/60 to 120/80, for patients in general and/or for a particular patient, and data analyzer 120 correlates the received verbal data signal to both the value 115/75 and the value 300/75, data analyzer 120 can record the value of 115/75 due to the bias in the algorithm toward the range 100/60 to 120/80. In some embodiments, the algorithm can be biased toward a previously received verbal data signal such as the last received verbal data signal. For example, if the last received verbal data signal includes a blood pressure reading of 115/75, and data analyzer 120 correlates the currently received verbal data signal to both the value 115/75 and the value of 300/75, data analyzer 120 can record the value of 115/75 due to a bias toward the value's proximity to the previously recorded value of 115/75.

Data analyzer 120 can identify and analyze verbal data signals recorded by input module 110. The verbal data signal can include patient data, such as data including but not limited to: ACT; blood pressure; heart rate; pulse rate; respiratory rate; glucose levels; saturated $O_2$ pressure; saturated $CO_2$ pressure; core body temperature; skin temperature; total lung capacity; residual volume; expiratory reserve volume; vital capacity; tidal volume; alveolar gas volume; actual lung volume; EEG bands such as Delta, Theta, Alpha, Beta, Gamma and Mu; EKG information such as RR interval, P wave length/amplitude, PR interval, amplitude of QRS complex, J-point detection, absolute and relative refractory periods, QT interval, and U & J Wave detection; blood volume; extra embolic gases; heparin volume; protamine sulfate volume; and combinations of these. Recorded data may be associated not only with a parameter level but a recording time. For example, the verbal communication "blood pressure is 150 over 90" can be identified by data analyzer 120 as 'blood pressure=150/90 @ time'. If an operator, such as the patient's primary caregiver (e.g. the surgeon), has specified that this parameter should be communicated by an operator associated with the verbal communication, then when that operator states the proper information, the stated value can be logged into memory module 150 with a time stamp.

Data analyzer 120 can identify verbal data signals including equipment data such as data including but not limited to: instructions to turn a piece of equipment on or off; instructions to modify the settings of one or more pieces of equipment; and combinations of these. Data analyzer 120 can identify non-verbal data signals including equipment data, such as audio data recorded from a piece of equipment (e.g. audio data recorded by a microphone of audio recorder 115), visual data recorded from a piece of equipment (e.g. visual data recorded by a camera of non-audio recorder 116), or electronic data output by a piece of equipment (e.g. via a wired or wireless communication between a piece of equipment and non-audio recorder 116).

Data analyzer 120 can identify verbal data signals including procedural data, such as procedural data selected from the group consisting of: total procedural length; length of a procedural step; time of initiation of a procedural step; time since last administration of a drug or other agent (e.g. time since infusion of heparin, protamine sulfate and/or cardioplegia); and combinations of these. Procedural steps include but are not limited to: patient preparation; anesthesia induction; opening/sternotomy; initiation of bypass; cardiac repair; termination of bypass; closure; post-op; anesthesia; insufflation; laparoscopic insertion such as laparoscopic insertion prior to a cholecystectomy; diagnosis confirmation; port incisions; removing bile; grasping a structure such as a gallbladder; isolating and dividing structures; separation of a first structure from a second structure such as a gallbladder from a liver; removal of a structure such as a gallbladder; irrigation such as abdominal wall irrigation; prostatectomy such as a robotic prostatectomy; docking of a robot; dissection such as SV dissection; hemostasis; completion of anastamosis; removal of drapes; and combinations of these.

Data analyzer 120 can identify a request for data from an operator recorded by audio recorder 115. Data requests can in a request for data selected from the group consisting of: a patient parameter; a procedural parameter; an equipment parameter; external data; patient historic data; and combinations of these. System 10 can be configured to respond to an operator's request quantitatively and/or qualitatively via output module 130. For example, an operator, e.g. the primary surgeon, can request the patient's blood pressure during a procedure, and system 10 will retrieve the patient parameter from the memory module and deliver the requested value to the operator, for example via an operator-worn headset or a visual display.

Data analyzer 120 can be configured to identify and/or require an acknowledgment of receipt of data. When a value is delivered to an operator, either pursuant to an impromptu request or the customized cadence input into input module 110, data analyzer 120 can identify the acknowledgement of receipt of the data based on a library of acceptable responses. For example, prior to a procedure being performed on a patient, a library of acceptable acknowledgement responses can be entered into input module 110, including but not limited to responses such as, "yeah", "yes", "okay", "gotcha", "thanks", and the like.

Data analyzer 120 can correlate the verbal data signal to a particular operator, for example using voice data entered into input module 110 prior to the procedure. In some embodiments, data analyzer 120 comprises an algorithm where the algorithm performs a first analysis on a verbal data signal correlated to a first operator and a second, different analysis on a verbal data signal correlated to a second operator. In some embodiments, data analyzer 120 correlates the verbal data signal of the first operator based on a first identifier and correlates the verbal data signal of the second operator based on a second, different identifier, for example where a headset worn by the first and second operators includes the identifier, such as an embedded electronic ID. In one example, the identifier can include a SIM card included in each headset worn by the first and second operator. These embodiments can apply to a clinical environment including one or multiple operators. Additionally, data analyzer 120 can correlate the verbal data signal to a particular operator type, each type comprising one or more operators of system 10. Operator types can include but are not limited to: a surgeon; an anesthesiologist; a scrub nurse; a circulating nurse; a hospital administrator; a patient; and combinations of these. Data analyzer 120 can employ an algorithm that determines an adverse condition has occurred based on the particular operator and/or operator type providing data via audio recorder 115 and/or another component of input module 110.

Data analyzer 120 can be configured to filter and/or segregate verbal data signals that are received by an operator. The verbal data signals can be filtered based on operator hierarchy and/or the importance of a particular value based on data entered into input module 110 prior to or during the procedure. For example, if a surgeon operator customizes system 10 such that a nurse or anesthesiologist operator should recite blood pressure readings every five minutes, data analyzer 120 can filter the nurse's speech based upon the value it is seeking, i.e. identify the nurse's recitation of blood pressure readings every five minutes. In instances where a desired reading is not identified in the predetermined time period (e.g. five minutes), system 10 can be configured to request the information, such as via output module 130.

Data analyzer 120 analyzes the verbal data signal recorded by audio recorder 115 to detect at least one adverse condition. In some embodiments, the verbal data signal is analyzed and/or compared to additional data entered into input module 110, as discussed above, such as data stored in memory module 150. In some embodiments, the adverse condition can be detected based on an analysis of the verbal data signal whose output exceeds a threshold. For example, if an operator entered a maximum acceptable value for the patient's blood pressure into input module 110, the data analyzer 120 will detect an adverse condition if the maximum acceptable value is exceeded.

In some embodiments, the adverse condition can be detected based on the identification of a keyword in the verbal data signal. In some embodiments, the adverse condition can be detected based on the identification of an unrecognized term or value in the verbal data signal. In some embodiments, the adverse condition can be detected based on the identification of an unrecognized or inaudible voice in the verbal data signal. In some embodiments, the adverse condition can be detected based on a determination that a particular operator has been active and/or present in the clinical environment past a threshold of time. For example, when an operator is the surgeon, data analyzer 120 can determine that the surgeon has been performing a complex procedure for a length of time that has been previously determined to exceed a safety threshold. The length of an operator's presence can be determined by data analyzer 120 receiving a verbal data signal and/or a video data signal from the particular operator, thus associating the receipt of the signal with the operator's presence. Additionally or alternatively, the operator's presence can be determined automatically, for example by a motion sensor, or manually, for example by a timecard entry assembly.

In some embodiments, the adverse condition can be detected based on the heightened frequency of recognized terms at a time other than that customized by the operator. In some embodiments, the adverse condition can be detected based on the non-receipt of information such as when an identified operator does not provide a particular piece of information at the proper time. In some embodiments, the adverse condition can be detected based on a determination that multiple pieces of similar data have not been received within a pre-determined time interval where the time interval can be an operator adjustable time interval that can be adjusted prior to and/or during a procedure. In some embodiments, the adverse condition can be detected based on a determination that a particular operator is not present. In some embodiments, the adverse condition can be detected based on an analysis of patient historic data and/or based on an analysis of a set of medical statistics such as a comparison of patient historic data to a set of medical statistics. In some embodiments, an adverse condition can be detected based on the identification of the patient's voice and/or gestures. For example, if the patient is no longer fully anesthetized and is able to speak and/or move, the data analyzer 120 can identify the patient's speech. In some embodiments, a library of evidence-based practices, for example a proper protocol or set of standards for a particular type of medical procedure can be entered into input module 110 prior to or during a procedure, where the real-time events occurring during the procedure can be recorded and compared and/or analyzed according to the evidence based information. An adverse event can be detected by data analyzer 120 when an event is detected that falls outside of the proper protocol or acceptable set of standards.

Output module 130 can include alert module 135 configured to alert at least one operator upon the detection of at least one adverse condition by data analyzer 120. Alert module 135 can alert one or all operators in the clinical environment, and any number of operators in between. In some embodiments, alert module 135 can be configured to alert a specific operator based on a unique identifier, for example an identifier included in that specific operator's headset, as discussed hereabove. In one embodiment, alert module 135 can include an audio transducer configured to produce an audible beep when an adverse condition is detected. The audible beep can include a first audible pattern associated with a first adverse condition, and a second, different audible pattern associated with a second, different adverse condition. In addition or alternative to an audible beep, the audio transducer can produce voice alert such as a computer generated voice or a recording of a human voice. Additionally or alternatively, alert module 135 can include a visual display, for example a visual display that provides alphanumeric text and/or graphic images when an adverse condition is detected. Additionally or alternatively, alert module 135 can include a tactile transducer such as an operator-worn tactile transducer and/or a vibrating transducer. Non-limiting examples of additional or alternative alert modules include: an audio transducer such as speaker and a piezo transducer; a visual transducer such as an LCD screen, a touch screen, and a light such as an LED; and a tactile transducer such as a vibrating transducer and a thermal transducer.

In addition to alert module 135, output module 130 may include numerous output components, such as to provide both alert and non-alert information to an operator of system 10. Output module 130 can be configured to provide an analysis of information to one or more operators such as patient and/or procedural information in real-time, i.e. during a procedure, or after completion of a procedure. In some embodiments, the information provided by output module 130 is information requested by at least one operator, for example information after the completion of a procedure in order to evaluate the overall performance of the operators as well as the relationship between team behavior and real-time changes in patient status. Additionally, a full audio transcript of the entire procedure can be provided and/or for each individual operator. Other types of information can be provided such as information selected from the group consisting of: a current (real-time) parameter; a historic parameter; an average of multiple parameter values; a maximum of multiple parameter values; and combinations of these. Other information can include one or more of: one or more adverse conditions detected; an operator's entry and/or exit time into the clinical setting; a procedure event that surpasses a threshold; an evidence-based decision support reminder; a captured video; a recommendation generated by the data analyzer; and combinations of these. The information can be provided to at least one operator or all operators in the form of a generated report, for example a hard copy and/or an electronic report. In some cases, system 10 can refer to a library of evidence-based practices, for example a library of data entered into input module 110, and system 10 can perform a quantitative or qualitative calculation related to clinical approach efficacy, appropriateness and/or timeliness. The report can then be transferred to a healthcare information system. Additionally, output module 130 can create a post-operative debrief in the form of an interactive montage of critical events, for example an output including procedure video, audio, transcripts of audio, patient vital signs during the procedure, corresponding pre-operative thresholds/scores, any relevant medical imaging, and any other desired information.

Data analyzer 120 can further include a data monitoring algorithm that confirms proper information is received by audio recorder 115, non-audio recorder 116, sensor 117, and/or data analyzer 120. Additionally, the data monitoring algorithm can confirm that proper information is received within one or more predetermined time intervals. The lack of receipt of information can lead to detection of an adverse event by data analyzer 120, such as has been described hereabove.

In addition to audio recorder 115 and non-audio recorder 116, input module 110 may include at least one sensor 117. Sensor 117 can comprise a sensor selected from the group consisting of: a temperature sensor; an acoustic sensor; an electromagnetic sensor; a pressure sensor; a motion sensor; and combinations of these. Output of these sensors may be included in one or more analyses of data analyzer 120, such as to determine if an adverse event has occurred or to produce other calculated data.

System 10 can further comprise a treatment device, such as treatment device 200 as shown in FIG. 1. In some embodiments, treatment device 200 comprises a device selected from the group consisting of: scalpel; electrocautery device; grasper; guidewire; interventional catheter; anesthesia injection device; RF or cryogenic ablation equipment; retractor; ECMO device; ventricular assist device; ventilator; bone awl; bone tamper; bone gouge; bone files; bone mallet; osteotome; defibrillator; drills; radiosurgery system; CPB machine; endoscope; cross clamp; robotic surgical system; colonoscope; polytectomy snare; and combinations of these. In some embodiments, treatment device 200 can comprise one or more electronic components or assemblies that can deliver information to input module 110 and/or receive control data from output module 130. In some embodiments, treatment device 200 can be modified or disabled upon the detection of an adverse event, for example an adverse event related detected by data analyzer receiving an equipment data signal.

Alert module 135 and other components of output module 130 can include numerous forms of user output components, such as components selected from the group consisting of: visual display such as an alphanumeric color display monitor; touchscreen display; indicator light such as an LED; audio transducer such as a speaker or piezo alert; tactile transducer such as an operator-worn assembly configured to vibrate on demand; USB port; wireless transmitter; internet connection; and combinations of these.

System 10 can further comprise a checklist. In some embodiments, data analyzer 120 can detect an adverse condition based upon an analysis of the checklist. The checklist can include a pre-operative, intra-operative, and/or a post-operative checklist that can be automatically and/or manually initiated. The checklist can comprise at least a portion that can be customized, such as a customization associated with one or more operators of system 10. The customization can be performed at any time, such as a time just prior to the performance of a medical procedure using system 10.

Figure 2:
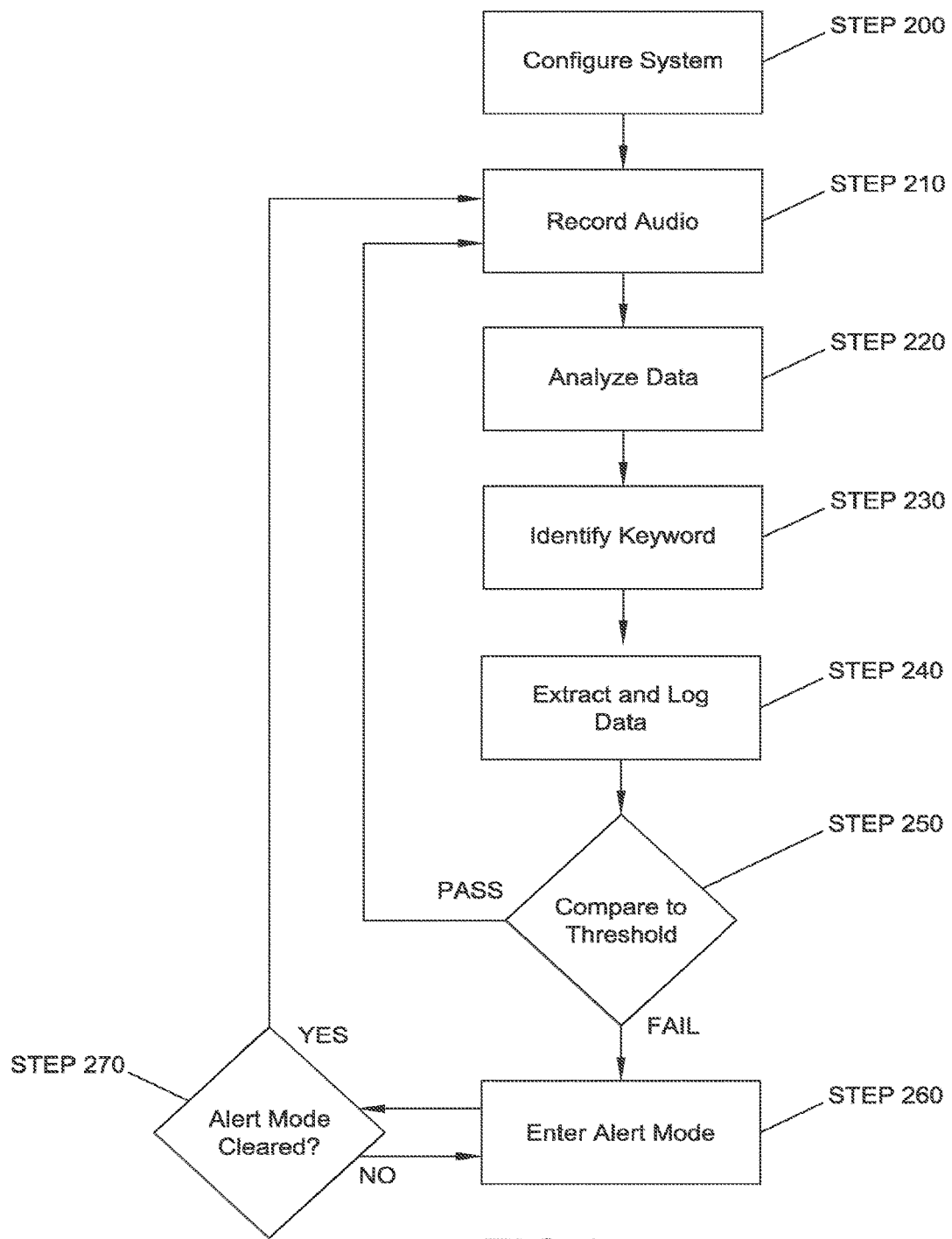
FIG. 2 illustrates a flow chart of a method for monitoring a medical procedure performed in a clinical environment, consistent with the present inventive concepts.

FIG. 2 illustrates a flow chart of a method for monitoring a medical procedure performed in a clinical environment, consistent with the present inventive concepts. The method includes configuring a system, for example system 10 of FIG. 1 hereabove, where the system is configured to produce a verbal data signal representative of verbal communication that occurs in the clinical environment; receive the verbal data signal and detect at least one adverse condition; and alert at least one operator when the at least one adverse condition is detected by the data analyzer.

The method may be performed during various types of medical procedures and may be performed in various clinical environments as described hereabove.

In STEP 200, the system is configured. Configuring the system can include entering data into an input module, for example, data entered into input module 110 as described in reference to FIG. 1 hereabove. In some embodiments, an operator can enter data into the input module at any time prior to, during, and/or subsequent to a medical procedure performed on a patient. The data entered can be updated, deleted, or otherwise modified at any time prior to, during, and/or subsequent to the procedure by any of the operators. In some embodiments, a specific operator can be authorized to enter, update, delete, or otherwise modify the input data.

The data input module can include one or more devices selected from the group consisting of: a keyboard; a touch screen; a motion-sensing input device; a mouse; a tablet; a cell phone; a handheld electronic organizer; a hospital computer or computer network; a wireless connection such as a cellular service; an internet connection; an electronic file transfer port such as USB port; a memory storage device such as a USB memory stick; and combinations of these. An application can be stored in one or more modules of the system enabling an operator to select a particular type and/or form of information to be communicated by the system to one or more operators. In some embodiments, an operator selects one or more patient and/or procedural parameters to be communicated and recorded by the system. Additionally, an operator can customize which particular operator should report the information and how frequently it should be reported by an operator and/or an output module such as output module 130 of FIG. 1. Furthermore, an operator can identify an adverse condition that should be detected by a data analyzer. In some embodiments, an operator can enter quantitative data into the input module such as a quantitative value for a threshold, where the data analyzer includes an algorithm configured to compare the threshold to a verbal data signal, as is described in STEP 250 below. An operator can enter a library of keywords associated with a parameter, such as a patient and/or procedural parameter that may be requested during a medical procedure, for example keywords that are typically associated with a patient and/or procedural parameter such as the keyword "blood pressure". Additionally, the primary user can enter a library of keywords associated with an adverse condition into the input module, where the data analyzer identifies the keywords, as has been described in reference to FIG. 1 hereabove.

Voice data can be entered into the input module, e.g. at least one spoken word, from each operator to be present during the medical procedure such that the data analyzer can identify an operator's voice based on the stored word or words.

External data which can include medical treatises, medical statistics, or any other medical information that is publicly or privately available can also be entered into the input module. The external data can be selected and/or filtered by an operator. For example, the operator can enter external information that is particularly relevant to the procedure to be performed or relevant to the particular patient's medical history and/or current medical status. Alternatively, entire treatises, books, or other medical sources can be entered into the input module.

Patient data, such as data including but not limited to, sex; age; height; weight; race; medical history; and combinations of these can also be entered into the input module.

In STEP 210, audio is recorded, for example via audio recorder 115 of FIG. 1. The audio recorder is configured to record a verbal communication and produce a verbal data signal that is representative of the verbal communication, for example via at least one microphone. The verbal communication can be a communication occurring prior to, during, and/or subsequent to a medical procedure. For example, a verbal communication occurring prior to a procedure can include input data being entered into the input module as described in STEP 200. A verbal communication occurring during a procedure can include but is not limited to: a notification of a patient, procedural and/or equipment parameter; a request for data; an acknowledgment of receipt of data; and combinations of these. The system can receive and/or transmit audio to each operator via the audio recorder, e.g. a headset worn by each operator, or the system can receive and/or transmit audio to a particular operator. Alternatively or additionally, the audio recorder can include an intercom system such that all operators can receive and/or transmit audio simultaneously.

Alternatively or additionally, video data can be recorded, for example via a video camera that can detect an operator gesture, for example a gesture including but not limited to a head nod or other affirmatory response; a head shake or other non-affirmatory response; a shrug; an indecisive response; and combinations of these. The video camera can also detect the speech of an operator. The gestures and/or speech are converted to a video data signal such that the video data signal can be analyzed by the data analyzer to detect an adverse condition. In some embodiments, an input module comprises a video camera and at least one microphone such that the data analyzer combines the verbal data signal with the video data signal and analyzes the combined signal. In cases where the verbal data is not heard, the data analyzer can analyze the video data signal to detect an adverse condition. Conversely, if the video data is not seen, the data analyzer can analyze the verbal data signal to detect an adverse event.

The recorded signals can be representative of a verbal communication received from a single operator and/or multiple operators. In the case of multiple operators, the system is configured to differentiate verbal data signals from a first operator and verbal data signals from a second operator. The verbal data signal can be representative of verbal communication occurring prior to, during, and/or after the medial procedure.

In some embodiments, non-verbal data signals are produced such as audio signals produced by a piece of equipment located in the clinical environment in the form of an equipment status signal, as has been described in reference to FIG. 1 hereabove.

In STEP 220, the data signals are analyzed, for example via data analyzer 120 of FIG. 1. The data analyzer can include spoken word recognition software employing at least one algorithm that converts the verbal data signal to text data. In some embodiments, the algorithm can be biased to correlate at least a portion of the verbal data signal to one or more medical terms where the system can further comprise a library of medical terms, where the algorithm's bias is based on the library of medical terms, as has been described in reference to FIG. 1 hereabove. The external data source can include medical treatises, medical statistics, or any other medical information that is publicly or privately available. Additionally, the data analyzer can include an algorithm configured to extract patient historic data from the data stored in a memory module. Further, the data analyzer can include an algorithm configured to extract the patient historic data stored in the memory module from the verbal data signal. Still further, the data analyzer can include an algorithm that is biased to correlate at least a portion of the verbal data signal to at least one quantitative value input by an operator. In some embodiments, the algorithm can be biased to a range of values, as has been described in detail hereabove. In some embodiments, the algorithm can be biased toward a previously received verbal data signal such as the last received verbal data signal, also described in detail hereabove.

The analysis can include an analysis of patient data; equipment data; procedural data; and combinations of these, examples of each provided hereabove.

The analysis can include an identification of a request for information, including but not limited to a request for a patient parameter; a procedural parameter; an equipment parameter; and combinations of these. The system is configured to respond to the operator's request quantitatively and/or qualitatively via the audio recorder. For example, an operator, e.g. the primary surgeon, can request the patient's blood pressure during a procedure, and the system will retrieve the patient parameter from the memory module and deliver the requested value to the operator, for example via an operator-worn headset and/or a visual display.

The analysis can include an identification of an acknowledgment of receipt of data. Alternatively or additionally, the analysis can identify when data has been provided to an operator and require that an acknowledgement be provided by the operator. As described above, a library of acceptable responses can be entered into an input module and the acknowledgement can be identified based upon the library.

The analysis can include a correlation of the verbal data signal to a particular operator, for example using the voice data entered into the input module prior to a procedure. In some embodiments, an algorithm performs a first analysis on a verbal data signal correlated to a first operator and a second, different analysis on a verbal data signal correlated to a second operator. In some embodiments, the correlation of a verbal data signal of the first operator is based on a first identifier and the correlation of the verbal data signal of the second operator is based on a second, different identifier, for example where a headset worn by the first and second operators includes the identifier, such as an embedded electronic ID. In one example, the identifier can include a SIM card included in each headset worn by the first and second operator. These embodiments can apply to a clinical environment including one, two, or multiple operators. Additionally, the analysis can include a correlation of the verbal data signal to a particular operator type, each type comprising one or more operators. Operator types can include but are not limited to a surgeon; an anesthesiologist; a scrub nurse; a circulating nurse; a hospital administrator; a patient; and combinations of these. An algorithm can be employed that determines an adverse condition has occurred based on the particular operator and/or operator type providing data via an audio recorder and/or other input module.

In STEP 230, one or more keywords are identified via the data analyzer. The identification can be based on a library of keywords associated with a parameter that may be requested during a medical procedure, for example keywords that are typically associated with a patient and/or procedural parameter such as the keyword "blood pressure". The library of keywords can be entered into the input module, for example by an operator prior to, during and/or subsequent to a procedure.

In STEP 240, data is extracted via the data analyzer. The data can be extracted based on operator hierarchy and/or the importance of a particular value based on data entered into an input module prior to, during and/or subsequent to the procedure. For example, if an operator customizes the system such that the nurse should recite blood pressure readings every five minutes, data analyzer can filter the nurse's speech based upon the value it is seeking, i.e. identify the nurse's recitation of blood pressure readings every five minutes. Additionally, the extracted data can be logged into the system such as recording and storing the data in a memory module with a time stamp.

In STEP 250, the extracted data is compared to a threshold, for example a threshold entered into an input module where the data analyzer includes an algorithm configured to compare the threshold to the data. In one embodiment, an adverse condition can be detected based on an analysis of the data exceeding a threshold. For example, if an operator entered a maximum acceptable value for the patient's blood pressure into the input module, the data analyzer will detect an adverse condition if the maximum acceptable value is exceeded.

If the data is within the acceptable limits, i.e. does not exceed a threshold, the method begins at STEP 210, and the steps are repeated. However, if the data exceeds the threshold, STEP 260 is performed where an alert mode is entered. In this step, an alert module, for example alert module 135 of FIG. 1 is configured to alert at least one operator. An alert can be provided to one or all operators in the clinical environment, and any number of operators in between. In some embodiments, an alert is provided to a specific operator based on a unique identifier, for example an identifier included in that specific operator's headset, as discussed hereabove. In one embodiment, an audible beep is produced when an adverse condition is detected. The audible beep can include a first audible pattern associated with a first adverse condition, and a second, different audible pattern associated with a second, different adverse condition. In addition or alternative to an audible beep, a voice alert such as a computer generated voice or a recording of a human voice can be produced. Additionally or alternatively, a visual display, for example a visual display that provides alphanumeric text and/or graphic images when an adverse condition is detected can be provided. Additionally or alternatively, a tactile transducer such as an operator-worn tactile transducer and/or a vibrating transducer can be included to alert at least one operator. Non-limiting examples of additional or alternative alert modules include: an audio transducer such as a speaker and a piezo transducer; a visual transducer such as an LCD screen, a touch screen, and a light such as an LED; and a tactile transducer such as a vibrating transducer and a thermal transducer.

In STEP 270, the alert mode is cleared, and if cleared, then the method begins at STEP 210, and the steps are repeated. The system will remain in the alert mode until cleared. The alert mode can be cleared by remedying any of the adverse conditions described herein.

In some embodiments, the alert module can be configured so as to automatically reset a threshold value if the alert mode is ignored. For example, if an adverse condition is detected based upon a blood pressure reading of 150/80, exceeding the threshold value of 145/75, the system will enter an alert mode. Continuing with this example, if the alert is ignored three times, the threshold value will reset to 150/80 or some value higher than its previous value. Statistical Process Control (SPC) can be used to handle error detection, or monitor alerts and any ignoring of alerts, such as to modify a threshold for entering an alert state after an alert is ignored a number of times.

The method can further comprise storing any of the data entered into the input module, as well as any verbal data signals that are received and/or processed, i.e. analyzed by the data analyzer, during a procedure, for example via a memory module.

In some embodiments, the method further comprises detecting an adverse condition based on the identification of a keyword in the verbal data signal. In some embodiments, the adverse condition can be detected based on the identification of an unrecognized term or value in the verbal data signal. In some embodiments, the adverse condition can be detected based on the identification of an unrecognized or inaudible voice in the verbal data signal. In some embodiments, the adverse condition can be detected based on a determination that a particular operator has been active and/or present in the clinical environment past a threshold of time. For example, when an operator is the surgeon, the data analyzer can determine that the surgeon has been performing a complex procedure for a length of time that has been previously determined to exceed a safety threshold. The length of an operator's presence can be determined by the data analyzer receiving a verbal data signal and/or a video data signal from the particular operator, thus associating the receipt of the signal with the operator's presence. Additionally or alternatively, the operator's presence can be determined automatically, for example by a motion sensor, or manually, for example by a timecard entry assembly. In some embodiments, the adverse condition can be detected based on the heightened frequency of recognized terms at a time other than that customized by the operator. In some embodiments, the adverse condition can be detected based on the non-receipt of information such as when an identified operator does not provide a particular piece of information at the proper time. In some embodiments, the adverse condition can be detected based on a determination that multiple pieces of similar data have not been received within a pre-determined time interval where the time interval can be an operator adjustable time interval that can be adjusted prior to and/or during a procedure. In some embodiments, the adverse condition can be detected based on a determination that a particular operator is not present. In some embodiments, the adverse condition can be detected based on an analysis of patient historic data and/or based on an analysis of a set of medical statistics such as a comparison of patient historic data to a set of medical statistics. In some embodiments, the adverse condition can be detected based on the identification of the patient's voice and/or gestures. For example, if the patient is no longer fully anesthetized and is able to speak and/or move, the data analyzer can identify the patient's speech. In some embodiments, a library of evidence-based practices, for example a proper protocol or set of standards for a particular type of medical procedure can be entered into the input module prior to or during a procedure, where the real-time events occurring during the procedure can be recorded and compared and/or analyzed according to the evidence based information. An adverse event can be detected by the data analyzer if an event is detected that falls outside of the proper protocol or acceptable set of standards. In some embodiments, the adverse condition can be detected based upon an analysis of a checklist. For example, the checklist can include a pre-operative, intra-operative, and/or a post-operative checklist that can be automatically and/or manually initiated. The checklist can be modified or include a portion that is modified or customized for a particular operator or set of operators.

The method can further comprise providing an analysis of information to one or more operators such as patient and/or procedural information in real-time, i.e. during a procedure, or after completion of a procedure. In some embodiments, the information is provided by an output module for example information requested by at least one operator, such as information after the completion of a procedure in order to evaluate the overall performance of the operators, as well as the relationship between team behavior and real-time changes in patient status. Additionally, a full audio transcript of the entire procedure can be provided and/or a transcript for each individual operator can be provided. Other types of information can be provided such as information selected from the group consisting of: a current (real-time) parameter; a historic parameter; an average of multiple parameter values; a maximum of multiple parameter values; and combinations of these. Other information can include one or more adverse conditions detected; an operator's entry and/or exit time into the clinical setting; a procedure event that surpasses a threshold; an evidence-based decision support reminder; a captured video; a recommendation generated by the data analyzer; and combinations of these. The information can be provided to at least one operator or all operators in the form of a generated report, for example a hard copy and/or an electronic report. In some cases, the system can refer to a library of evidence-based practices, for example a library of data entered into the input module, and the system can discern whether the clinical approach was efficacious, appropriate and done in a timely manner. The report can then be transferred to a healthcare information system. Additionally, output module can create a post-operative debrief in the form of an interactive montage of critical events, for example an output including procedure video, audio, transcripts of audio, patient vital signs during the procedure, corresponding pre-operative thresholds/scores, any relevant medical imaging, and any other desired information.

The method can further comprise confirming proper information is received by the audio recorder and/or the data analyzer, for example via a data monitoring algorithm. Additionally, a confirmation that proper information is received by the audio recorder and/or the data analyzer within one or more predetermined time intervals can be performed. The lack of receipt of information can lead to the detection of an adverse event, as has been described hereabove.

The method can further comprise sensing at least one adverse condition via at least one sensor, for example a sensor such as a temperature sensor; an acoustic sensor; an electromagnetic sensor; a pressure sensor; a motion sensor; and combinations of these.

In some embodiments, the method further comprises communicating with a healthcare information system, for example the input module can receive information from the healthcare information system such as information relevant to the particular patient and/or procedure to be performed, for example patient historic data. Similarly, the data provided by the output module can be communicated to the healthcare information system.

The method can further comprise treating a patient via a treatment device, for example treatment device 200 described in reference to FIG. 1 hereabove.

Figure 3:
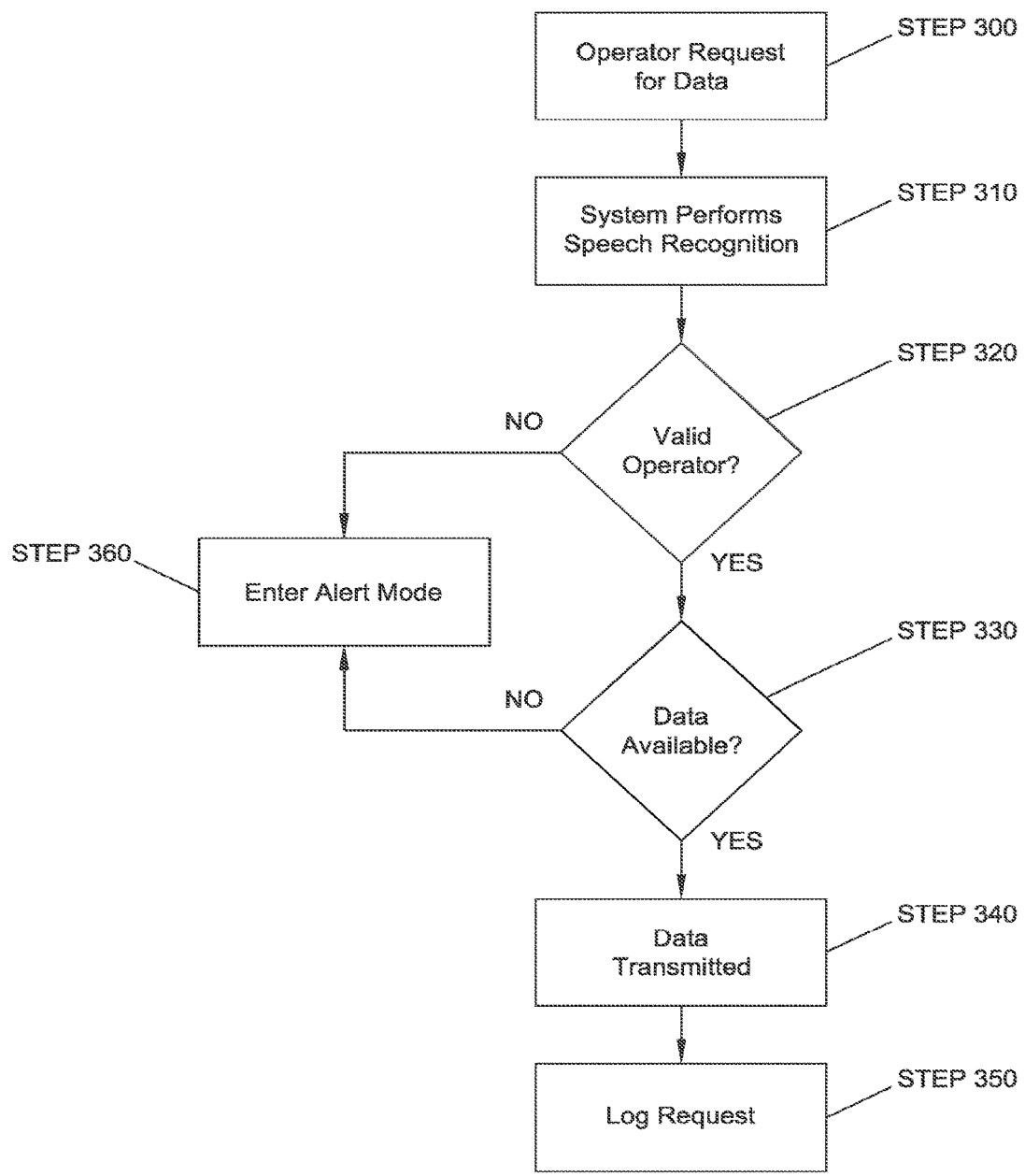
FIG. 3 illustrates a flow chart of a method of requesting data during a medical procedure performed in a clinical environment, consistent with the present inventive concepts.

FIG. 3 illustrates a flow chart of a method for requesting data during a medical procedure performed in a clinical environment, consistent with the present inventive concepts. In STEP 300, an operator makes a request for data, for example a patient, procedural, and/or an equipment parameter. Additionally, other data can be requested, for example patient historic data and external data such as medical statistics. Typically, the request includes a verbal request for data, where an audio recorder, for example audio recorder 115 of FIG. 1 converts the verbal request to a verbal data signal.

In STEP 310, a speech recognition step is performed. In some embodiments, speech recognition software comprising an algorithm performs an analysis on the received verbal data signal and correlates the verbal data signal to the specific operator. In some embodiments, the correlation of the verbal data signal of the operator is based on an identifier, for example where a headset worn by the operator includes the identifier. In one embodiment, the identifier can include a SIM card included in the operator's headset.

In STEP 320, a confirmation that the operator requesting the data is a valid operator is performed. In one embodiment, the validity of the operator is confirmed based on the data an operator entered into an input module such as input module 110 of FIG. 1. For example, an operator can authorize a particular operator to make a request for a particular type or types of data. In an example, if the surgeon requests data during the procedure, a data analyzer, for example data analyzer 120 of FIG. 1, can identify the surgeon's speech and determine if it is in fact the surgeon requesting the data. As discussed above, the data analyzer can comprise speech recognition software employing an algorithm to detect the operator's speech, in this case the surgeon, or alternatively, the surgeon can wear a headset comprising an identifier such as a SIM card.

The system can also be configured more narrowly, for example, by designating both a valid operator and correlating that operator to a particular piece of data, such as a particular patient parameter. For example, if the primary user customizes the system such that the nurse shall provide and/or request blood pressure readings, the data analyzer can identify the nurse's speech and determine if it is in fact the nurse requesting and/or providing the blood pressure reading. As discussed above, the data analyzer can comprise speech recognition software employing an algorithm to detect the operator's speech, in this case the nurse, or alternatively, the nurse can wear a headset comprising an identifier such as a SIM card.

If the operator is determined to be a valid operator, a check for the requested data is performed, as shown in STEP 330. As described in STEP 230 240 of FIG. 2, when an operator verbally communicates data, a value associated with the data is logged into a memory module, for example memory module 150 of FIG. 1, with a time stamp. For example, the verbal communication "blood pressure is 150 over 90" will be identified by the data analyzer as 'blood pressure=150/90 @ time'. If an operator has specified that this parameter should be communicated by the operator associated with the verbal communication, the then value is logged into a memory module with a time stamp, and then can be retrieved and transmitted, as shown in STEP 340 described below.

However, if the operator is determined to be an invalid operator and/or the requested data is not stored in the memory module, an alert mode will be entered as shown in STEP 360. The alert mode is similar to that described in STEP 260 of FIG. 2 hereabove.

Once the operator is determined to be a valid operator and the requested data has been retrieved from the memory module, STEP 340 can be performed where the requested data is transmitted to the requesting operator. In one embodiment, each operator wears a headset, and requested data can be transmitted to the requesting operator's headset. In some embodiments, each headset comprises a unique identifier associated with each operator such that the data analyzer can correlate a verbal data signal to a specific operator, for example an identifier such as a SIM card. In some embodiments, speech recognition software comprising an algorithm performs an analysis on the received verbal data signal and correlates the verbal data signal to the requesting operator via a headset worn by that operator. In some embodiments, the requested data can be transmitted to other operators in addition to the requesting operator, for example two or all operators in the clinical environment. The information can be transmitted to the operator(s) via a headset. Alternatively or additionally, the information can be transmitted via an intercom system and/or a visual display such that all operators can receive and/or transmit audio simultaneously.

In STEP 350, the request for data is logged, for example in the memory module. An output module, such as output module 130 of FIG. 1, can produce a report providing data related to the requests made during a procedure, for example the total number of requests made.

Figure 4:
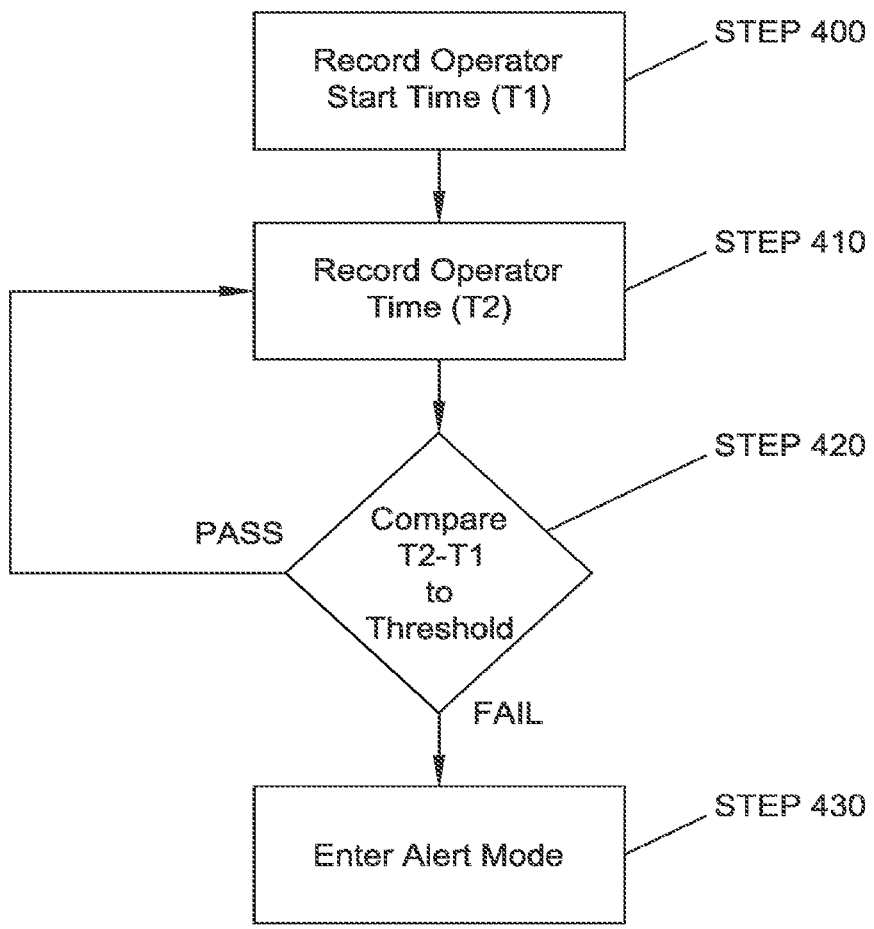
FIG. 4 illustrates a flow chart of a method for monitoring the presence of an operator during a medical procedure performed in a clinical environment, consistent with the present inventive concepts.

FIG. 4 illustrates a flow chart of a method for monitoring the presence of an operator during a medical procedure performed in a clinical environment, consistent with the present inventive concepts. In one embodiment, the illustrated method can be performed to monitor the presence of a surgeon during a procedure to ensure that the surgeon is not active and/or performing surgery past a threshold value. The illustrated method can be performed for multiple operators during a procedure.

In STEP 400, a start time T1 of an operator is recorded and logged into a memory module, for example the memory module, as has been described herein. In one embodiment, a data analyzer, for example data analyzer 120 of FIG. 1 receives a verbal data signal and/or a video data signal from an audio recorder, for example audio recorder 115110 of FIG. 1, thus associating the receipt of the signal with the operator's presence. The first verbal data signal can roughly represent the operator's start time T1. Additionally or alternatively, the operator's start time can be determined automatically, for example by a motion sensor, or manually, for example by a timecard entry assembly.

In STEP 410, the operator's time at T2 is recorded and logged into the memory module. T2 can be recorded and logged similarly to T1.

In STEP 420, the operator's presence, represented by the value equaling T2 minus T1, is compared to a threshold. The threshold value can be a value that is predetermined for patient safety based upon the complexity of the procedure being performed. In the example where the operator is the surgeon, the threshold value can be determined based upon the ability and/or experience of the surgeon; whether or not the surgeon has performed other procedures within a particular amount of time such as within the last eight hours; the length of time the surgeon has performed the current procedure without a relief; whether or not the assistant surgeon has left early or during a critical phase; and combinations of these. The threshold value can be entered into an input module, for example input module 110 of FIG. 1, prior to a procedure, as has been described hereabove.

If the operator's presence, i.e. T2 minus T1, does not exceed a threshold value, the steps can be repeated, beginning with STEP 410. However, if the operator's presence does exceed a threshold value, an alert mode will be entered as shown in STEP 430. The alert mode is similar to that described in STEP 260 of FIG. 2 hereabove.

The foregoing description and accompanying drawings set forth a number of examples of representative embodiments at the present time. Various modifications, additions and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

We claim:

1. A system for monitoring a medical procedure performed in a clinical environment comprising:
    an audio recorder constructed and arranged to produce a verbal data signal representative of verbal communication that occurs in the clinical environment;
    a data analyzer constructed and arranged to receive the verbal data signal from the audio recorder, analyze the verbal data signal and detect at least one adverse condition; and
    an alert module constructed and arranged to alert at least one operator when the at least one adverse condition is detected by the data analyzer,
    wherein the data analyzer comprises a threshold, and wherein the detection of the at least one adverse condition is based on data extracted from the verbal data signal exceeding the threshold.

2. The system of claim 1 wherein the medical procedure comprises a procedure selected from the group consisting of: a surgical procedure; a laparoscopic surgical procedure; an open surgical procedure; an interventional procedure; a reconstructive surgery; a robotic or robotically-enabled procedure; an outpatient procedure; a dental procedure; and combinations thereof.

3. The system of claim 1 wherein the clinical environment comprises a setting selected from the group consisting of: an operating room; a catheterization lab; an intensive care unit; a control room for an operating room; an outpatient surgery treatment room; a dentist's office; a surgeon's office, such a maxillofacial surgeon's office; and combinations thereof.

4. The system of claim 1 wherein the audio recorder comprises at least one microphone.

5. The system of claim 1 wherein the audio recorder comprises multiple microphones.

6. The system of claim 5 wherein the multiple microphones are in proximity to the at least one operator.

7. The system of claim 5 wherein the multiple microphones comprise a first microphone positioned in proximity to a first operator and a second microphone in proximity to a second operator.

8. The system of claim 1 wherein the audio recorder is selected from the group consisting of: a microphone; an operator-worn microphone or headset; a room microphone; an omnidirectional microphone; a Bluetooth device; a telephone; a mobile telephone; a wireless device; and combinations thereof.

9. The system of claim 1 wherein the audio recorder comprises an operator-worn headset.

10. The system of claim 9 wherein each operator of the at least one operators wears a headset.

11. The system of claim 10 wherein each headset comprises an identifier associated with the operator.

12. The system of claim 1 wherein the audio recorder comprises an intercom system.

13. The system of claim 1 wherein the audio recorder is further constructed and arranged to produce a non-verbal data signal.

14. The system of claim 13 wherein the non-verbal data signal comprises audio signals produced by equipment positioned in the clinical environment.

15. The system of claim 14 wherein the data analyzer is further constructed and arranged to receive the non-verbal data signal from the audio recorder, analyze the non-verbal data signal and detect an equipment status signal.

16. The system of claim 15 wherein the equipment status signal comprises an equipment warning signal.

17. The system of claim 1 further comprising a video camera constructed and arranged to produce a video data signal.

18. The system of claim 17 wherein the data analyzer is constructed and arranged to receive the video data signal from the video camera and analyze the video data signal.

19. The system of claim 18 wherein the data analyzer is further constructed and arranged to detect an operator gesture.

20. The system of claim 19 wherein the operator gesture comprises a gesture selected from the group consisting of: a head nod or other affirmatory response; a head shake or other non-affirmatory response; a shrug; an indecisive response; and combinations thereof.

21. The system of claim 18 wherein the data analyzer is further constructed and arranged to detect at least one spoken word in the video data signal.

22. The system of claim 18 wherein the data analyzer is further constructed and arranged to detect at least one adverse condition in the video data signal.

23. The system of claim 17 wherein the data analyzer is constructed and arranged to combine the verbal data signal and the video data signal to produce a combined signal and to analyze the combined signal.

24. The system of claim 17 wherein the data analyzer is constructed and arranged to combine and analyze the verbal data signal and the video data signal, and to detect an adverse condition based on the combined analysis.

25. The system of claim 1 wherein the verbal data signal comprises communication data received from a single operator.

26. The system of claim 1 wherein the verbal data signal comprises communication data from at least a first operator and a second operator.

27. The system of claim 26 wherein the data analyzer is constructed and arranged to differentiate communication data of the first operator from communication data of the second operator.

28. The system of claim 1 wherein the verbal data signal comprises verbal communication that occurred prior to initiation of the medical procedure.

29. The system of claim 1 wherein the verbal data signal comprises verbal communication that occurred during the performance of the medical procedure.

30. The system of claim 1 wherein the verbal data signal comprises verbal communication that occurred after the performance of the medical procedure.

31. The system of claim 1 wherein the data analyzer comprises a component selected from the group consisting of: microprocessor; microcontroller; analog to digital converter; digital to analog converter; and combinations thereof.

32. The system of claim 1 wherein the data analyzer comprises spoken word recognition software employing at least one algorithm, wherein the algorithm converts the verbal data signal to text data.

33. The system of claim 32 wherein the at least one algorithm is biased to correlate at least a portion of the verbal data signal to one or more medical terms.

34. The system of claim 33 further comprising a library of medical terms and wherein the bias is based on the library of medical terms.

35. The system of claim 32 further comprising a library of medical terms.

36. The system of claim 32 wherein the at least one algorithm is biased to correlate at least a portion of the verbal data signal to one or terms input by an operator.

37. The system of claim 32 wherein the at least one algorithm is biased to correlate at least a portion of the verbal data signal to at least one quantitative value input by an operator.

38. The system of claim 37 wherein the at least one quantitative value comprises a range of values.

39. The system of claim 32 wherein the at least one algorithm is biased to correlate at least a portion of the verbal data signal to a range of quantitative values wherein the range comprises quantitative values that are typically associated with a parameter.

40. The system of claim 32 wherein the at least one algorithm is biased to correlate at least a portion of the verbal data signal to a previously received verbal data signal.

41. The system of claim 40 wherein the at least a portion of the verbal data signal comprises a quantitative value.

42. The system of claim 1 wherein the data analyzer comprises a memory module constructed and arranged to store patient historic data.

43. The system of claim 42 wherein the stored patient data comprises data selected from the group consisting of: sex; age; height; weight; race; medical history; and combinations thereof.

44. The system of claim 42 wherein the data analyzer comprises an algorithm to extract the patient historic data from the verbal data signal.

45. The system of claim 42 wherein the system further comprises in input device constructed and arranged to allow an operator to enter the patient historic data.

46. The system of claim 45 wherein the input device comprises a device selected from the group consisting of: a keyboard; a touch screen display; and combinations thereof.

47. The system of claim 1 wherein the data analyzer is constructed and arranged to identify patient data in the verbal data signal.

48. The system of claim 47 wherein the patient data is selected from the group consisting of: ACT; blood pressure; heart rate; pulse rate; respiratory rate; glucose levels; saturated O2 pressure; saturated CO2 pressure; core body temperature; skin temperature; total lung capacity; residual volume; expiratory reserve volume; vital capacity; tidal volume; alveolar gas volume; actual lung volume; EEG bands comprising Delta, Theta, Alpha, Beta, Gamma and Mu; EKG information comprising RR interval, P wave length/amplitude, PR interval, amplitude of QRS complex, J-point detection, absolute and relative refractory periods, QT interval and U & J Wave detection; blood volume; extra embolic gases; heparin volume; protamine sulfate volume; and combinations thereof.

49. The system of claim 1 wherein the data analyzer is constructed and arranged to identify equipment data in the verbal data signal.

50. The system of claim 49 wherein the equipment data is selected from the group consisting of: instructions to turn a piece of equipment on or off; instructions to modify at least one setting of one or more pieces of equipment; and combinations thereof.

51. The system of claim 1 wherein the data analyzer is constructed and arranged to identify procedure data in the verbal data signal.

52. The system of claim 51 wherein the procedure data is selected from the group consisting of: total procedure length; length of a procedural step; time of initiation of a procedural step; time since last administration of a drug or other agent; and combinations thereof.

53. The system of claim 52 wherein the procedural steps are selected from the group consisting of: patient preparation; anesthesia induction; opening/sternotomy; initiation of bypass; cardiac repair; termination of bypass; closure; post-op; anesthesia; insufflation; laparoscopic insertion; diagnosis confirmation; port incisions; removing bile; grasping a structure; isolating and dividing structures; separation of a first structure from a second structure; removal of a structure; irrigation; prostatectomy; docking of a robot; dissection; hemostasis; completion of anastamosis; removal of drapes; and combinations thereof.

54. The system of claim 1 wherein the data analyzer is constructed and arranged to identify a request for information data in the verbal data signal.

55. The system of claim 54 wherein the request for information data comprises a request for information selected from the group consisting of: a patient parameter; a procedural parameter; an equipment parameter; and combinations thereof.

56. The system of claim 54 wherein the system is constructed and arranged to provide a quantitative and/or qualitative response to the request.

57. The system of claim 1 wherein the data analyzer is constructed and arranged to identify an acknowledgement of receipt of information.

58. The system of claim 57 further comprising a library of acknowledgement terms.

59. The system of claim 1 wherein the data analyzer is constructed and arranged to correlate the verbal data signal received to a first operator or to a second operator.

60. The system of claim 59 wherein the data analyzer comprises an algorithm for detecting the adverse condition, wherein the algorithm comprises a first analysis on data correlated to the first operator and a second, different analysis on data correlated to the second operator.

61. The system of claim 59 wherein the data analyzer correlates the verbal data signal of the first operator based on a first identifier and correlates the verbal data signal of the second operator based on a second identifier, wherein the first identifier is different from the second identifier.

62. The system of claim 61 wherein a headset worn by the first and second operators comprises the identifier.

63. The system of claim 1 wherein the data analyzer is constructed and arranged to correlate the verbal data signal to an operator type.

64. The system of claim 63 wherein the operator type comprises a function selected from the group consisting of: a surgeon; an anesthesiologist; a scrub nurse; a circulating nurse; hospital administrator; and combinations thereof.

65. The system of claim 63 wherein the data analyzer comprises an algorithm, and wherein the algorithm detects the adverse condition based on the operator type and the verbal data signal.

66. The system of claim 1 wherein the data analyzer is constructed and arranged to filter and/or segregate verbal data received from the at least one operator.

67. The system of claim 66 wherein the filtered and/or segregated verbal data is prioritized based on an operator hierarchy.

68. The system of claim 1 wherein the data analyzer is constructed and arranged to filter and/or segregate verbal data received from a non-operator.

69. The system of claim 1 wherein the data analyzer comprises a memory module.

70. The system of claim 69 wherein the memory module is constructed and arranged to store one or more portions of the verbal data signal.

71. The system of claim 69 wherein the memory module is constructed and arranged to store processed verbal data signal.

72. The system of claim 69 wherein the memory module is constructed and arranged to store a library of values.

73. The system of claim 72 wherein the library of values comprises multiple spoken word terms to be recognized.

74. The system of claim 72 wherein the library of values comprises one or more quantitative values, wherein the data analyzer comprises an algorithm which compares the verbal data signal to the one or more quantitative values.

75. The system of claim 69 wherein the memory module is constructed and arranged to store historic medical statistics and/or other medical data.

76. The system of claim 69 wherein the memory module is constructed and arranged to store one or more portions of a video data signal produced by a video camera.

77. The system of claim 1 wherein the threshold comprises a value or a range of values input to the system by an operator.

78. The system of claim 1 wherein the threshold comprises a value or a range of values relating to at least one of a patient, procedural or equipment parameter.

79. The system of claim 1 wherein the data analyzer is constructed and arranged to detect the at least one adverse condition based on an identification of a key word in the verbal data signal.

80. The system of claim 1 wherein the data analyzer is constructed and arranged to detect the at least one adverse condition based on a detection of an unrecognized voice in the verbal data signal.

81. The system of claim 1 wherein the data analyzer is constructed and arranged to detect the at least one adverse condition based on a detection of an unrecognized term in the verbal data signal.

82. The system of claim 1 wherein the data analyzer is constructed and arranged to detect the at least one adverse condition based on a determination that a first operator has been active and/or present above a threshold of time.

83. The system of claim 82 wherein the first operator comprises a surgeon.

84. A system for monitoring a medical procedure performed in a clinical environment comprising:
    an audio recorder constructed and arranged to produce a verbal data signal representative of verbal communication that occurs in the clinical environment;
    a data analyzer constructed and arranged to receive the verbal data signal from the audio recorder, analyze the verbal data signal and detect at least one adverse condition; and
    an alert module constructed and arranged to alert at least one operator when the at least one adverse condition is detected by the data analyzer,
    wherein the data analyzer is constructed and arranged to detect the at least one adverse condition based on a detection of a heightened frequency of recognized terms at an improper time.

85. The system of claim 1 wherein the data analyzer is constructed and arranged to detect the at least one adverse condition based on a lack of receipt of information.

86. The system of claim 1 wherein the data analyzer is constructed and arranged to detect the at least one adverse condition based on a determination that multiple pieces of similar data have not been received within a pre-determined time interval.

87. The system of claim 86 wherein the time interval comprises an operator adjustable time interval.

88. The system of claim 1 wherein the data analyzer is constructed and arranged to detect the at least one adverse condition based on a determination that a particular operator is not present.

89. The system of claim 1 wherein the data analyzer is constructed and arranged to detect the at least one adverse condition based on an analysis of patient historic data.

90. The system of claim 1 wherein the data analyzer is constructed and arranged to detect the at least one adverse condition based on an analysis of a set of medical statistics.

91. The system of claim 90 wherein the set of medical statistics is pre-selected by an operator.

92. The system of claim 1 wherein the alert module is constructed and arranged to notify a single operator of the detection of the at least one adverse condition.

93. The system of claim 92 wherein the alert module notifies a single operator based upon an identifier associated with the operator.

94. The system of claim 93 wherein a headset worn by the operator comprises the identifier.

95. The system of claim 1 wherein the alert module is constructed and arranged to notify multiple operators of the detection of the at least one adverse condition.

96. The system of claim 1 wherein the alert module comprises an audio transducer.

97. The system of claim 96 wherein the alert module is constructed and arranged to produce an audible beep when the at least one adverse condition is detected.

98. The system of claim 96 wherein the data analyzer is constructed and arranged to detect a first adverse condition and a second adverse condition, and wherein the audio transducer is constructed and arranged to produce a first audio pattern when the first adverse condition is detected and a second audio pattern when the second adverse condition is detected.

99. The system of claim 96 wherein the audio transducer is constructed and arranged to produce a sound selected from the group consisting of: a computer generated voice; a recording of a human voice; and combinations thereof.

100. The system of claim 1 wherein the alert module comprises a visual display.

101. The system of claim 100 wherein the visual display is constructed and arranged to provide alpha-numeric text when an adverse condition is detected.

102. The system of claim 1 wherein the alert module comprises a tactile transducer.

103. The system of claim 102 wherein the tactile transducer comprises an operator-worn tactile transducer.

104. The system of claim 102 wherein the tactile transducer comprises a vibrating transducer.

105. The system of claim 1 wherein the alert module comprises multiple alert transducers.

106. The system of claim 1 wherein the alert module comprises at least one alert transducer selected from the group consisting of: an audio transducer; a visual transducer; a tactile transducer; and combinations thereof.

107. The system of claim 1 further comprising a data input module constructed and arranged to allow at least one operator to input data to the system.

108. The system of claim 107 wherein the data input module comprises a voice data input module.

109. The system of claim 108 wherein the data input module comprises a microphone.

110. The system of claim 107 wherein the data input module comprises a text data input module.

111. The system of claim 110 wherein the data input module comprises a device selected from the group consisting of: a keyboard; a touch screen; a motion-sensing input device; a cell phone; a handheld electronic organizer; a mouse; a tablet; a hospital computer or computer network; a wireless connection; an internet connection; an electronic file transfer port; a memory storage device; and combinations thereof.

112. The system of claim 107 wherein the data input module is constructed and arranged to receive operator voice data from a first operator.

113. The system of claim 112 wherein the data analyzer is constructed and arranged to convert the verbal data signal to text data based on the received first operator voice data.

114. The system of claim 112 wherein the data analyzer is constructed and arranged to correlate the verbal data signal to the operator voice data to identify the operator.

115. The system of claim 107 wherein the data analyzer comprises memory, wherein the operator input data comprises spoken word terms, and wherein the data analyzer is constructed and arranged to store the spoken word terms in the memory.

116. The system of claim 115 wherein the data analyzer further comprises an algorithm, and wherein the algorithm comprises a comparison of the verbal data signal to the spoken word terms stored in the memory which converts the verbal data signal to text data.

117. The system of claim 107 wherein the data analyzer comprises memory, wherein the operator input data comprises quantitative data, and wherein the data analyzer is constructed and arranged to store the quantitative data in the memory.

118. The system of claim 117 wherein the data analyzer further comprises an algorithm, and wherein the algorithm comprises a comparison of the verbal data signal to quantitative data stored in the memory.

119. The system of claim 118 wherein the quantitative data stored in the memory comprises a threshold value used in the comparison.

120. The system of claim 107 wherein the data input module is constructed and arranged to receive information from a healthcare information system.

121. The system of claim 1 further comprising a data output module.

122. The system of claim 121 wherein the data output module is constructed and arranged to provide patient and/or procedural information to at least one operator.

123. The system of claim 122 wherein the patient and/or procedural information provided is in response to a request by the at least one operator.

124. The system of claim 122 wherein the patient and/or procedural information comprises information selected from the group consisting of: a current or real-time parameter; a historic parameter; an average of multiple parameter values; a maximum of multiple parameter values; and combinations thereof.

125. The system of claim 121 wherein the data output module is constructed and arranged to provide patient and/or procedural information in paper form.

126. The system of claim 121 wherein the data output module is constructed and arranged to provide patient and/or procedural information in electronic form.

127. The system of claim 121 wherein the data output module is constructed and arranged to provide information selected from the group consisting of: an adverse condition detected; an operator's entry and/or exit time into the clinical setting; a procedure event that surpasses a threshold; an evidence-based decision support reminder; a captured video; a recommendation generated by the data analyzer; and combinations thereof.

128. The system of claim 121 wherein the data output module is constructed and arranged to transfer information to a healthcare information system.

129. The system of claim 1 wherein the data output module is constructed and arranged to provide data in real-time.

130. The system of claim 1 wherein the data output module is constructed and arranged to provide data after completion of a procedure.

131. The system of claim 1 further comprising a data monitoring module.

132. The system of claim 131 wherein the data monitoring module is constructed and arranged to confirm proper information is received.

133. The system of claim 131 wherein the data monitoring module is constructed and arranged to confirm proper information is continually received within a pre-determined time interval.

134. The system of claim 1 further comprising an operator position monitoring module.

135. The system of claim 134 wherein the operator position monitoring module is constructed and arranged to monitor an operator position by detecting an operator voice in the verbal data signal.

136. The system of claim 134 wherein the operator position monitoring module comprises a motion sensor.

137. The system of claim 134 wherein the operator position monitoring module comprises a video camera.

138. The system of claim 134 wherein the operator position monitoring module comprises a timecard entry assembly.

139. The system of claim 1 further comprising at least one sensor.

140. The system of claim 139 wherein the at least one sensor comprises one or more sensors selected from the group consisting of: a temperature sensor; an acoustic sensor; an electromagnetic sensor; a pressure sensor; a motion sensor; and combinations thereof.

141. The system of claim 1 further comprising a patient treatment device.

142. The system of claim 141 wherein the treatment device is selected from the group consisting of: scalpel; electrocautery device; grasper; guidewire; interventional catheter; anesthesia injection device; RF or cryogenic ablation equipment; retractor; ECMO device; ventricular assist device; ventilator; bone awl; bone tamper; bone gouge; bone file; bone mallet; osteotome; defibrillator; drill; radiosurgery system; CPB machine; endoscope; cross clamp; robotic surgical system; colonoscope; polytectomy snare; and combinations thereof.

143. The system of claim 141 wherein the treatment device is modified if an adverse event is detected.

144. The system of claim 143 wherein the modification comprises a disabling or powering down of the treatment device.

145. The system of claim 1 further comprising a checklist wherein the data analyzer detects the at least one adverse condition based upon an analysis of the checklist.

146. The system of claim 145 wherein the checklist comprises at least a portion that is customized for a particular operator.

147. The system of claim 146 wherein the checklist is constructed and arranged to be customized prior to the performance of a medical procedure.

148. A method for monitoring a medical procedure performed in a clinical environment comprising:
producing a verbal data signal representative of verbal communication that occurs in the clinical environment;
receiving the verbal data signal;
analyzing the verbal data signal;
detecting at least one adverse condition; and
alerting at least one operator when the at least one adverse condition is detected,
wherein detecting the adverse condition is based on data extracted from the verbal data signal exceeding a threshold.

149. The method of claim 148 wherein the medical procedure comprises a procedure selected from the group consisting of: a surgical procedure; a laparoscopic surgical procedure; an open surgical procedure; an interventional procedure; a reconstructive surgery; a robotic or robotically-enabled procedure; an outpatient procedure; a dental procedure; and combinations thereof.

150. The method of claim 148 wherein the clinical environment comprises a setting selected from the group consisting of: an operating room; a catheterization lab; an intensive care unit; a control room for an operating room; an outpatient surgery treatment room; a dentist's office; a surgeon's office; a maxillofacial surgeon's office; and combinations thereof.

151. The method of claim 148 wherein producing the verbal data signal is via an audio recorder.

152. The method of claim 151 wherein the audio recorder is selected from the group consisting of: a microphone; an operator-worn microphone or headset; a room microphone; an omnidirectional microphone; a Bluetooth device; a telephone; a mobile telephone; a wireless device; and combinations thereof.

153. The method of claim 148 further comprising producing a non-verbal data signal.

154. The method of claim 153 wherein the non-verbal data signal comprises an equipment status signal, and wherein the method further comprises receiving the equipment status signal and detecting the equipment status signal.

155. The method of claim 153 further comprising receiving the non-verbal data signal and analyzing the non-verbal data signal.

156. The method of claim 148 further comprising producing a video data signal.

157. The method of claim 156 further comprising receiving the video data signal and analyzing the video data signal.

158. The method of claim 156 further comprising detecting an operator gesture wherein the operator gesture comprises a gesture selected from the group consisting of: a head nod or other affirmatory response; a head shake or other non-affirmatory response; a shrug; an indecisive response; and combinations thereof.

159. The method of claim 158 further comprising detecting at least one spoken word in the video data signal.

160. The method of claim 158 further comprising detecting at least one adverse condition in the video data signal.

161. The method of claim 158 further comprising combining the verbal data signal and the video data signal to produce a combined signal and analyzing the combined signal.

162. The method of claim 158 further comprising analyzing the verbal data signal and the video data signal and detecting an adverse condition based on the combined analysis.

163. The method of claim 148 wherein receiving the verbal data signal comprises receiving communication data from a single operator.

164. The method of claim 148 wherein receiving the verbal data signal comprises receiving data from at least a first operator and a second operator.

165. The method of claim 164 further comprising differentiating the communication data of the first operator from the communication data of the second operator.

166. The method of claim 148 wherein receiving the verbal data signal comprises receiving verbal communication that occurred prior to initiation of the medical procedure.

167. The method of claim 148 wherein receiving the verbal data signal comprises receiving verbal communication that occurred during the performance of the medical procedure.

168. The method of claim 148 wherein receiving the verbal data signal comprises receiving verbal communication that occurred after the performance of the medical procedure.

169. The method of claim 148 wherein analyzing the verbal data signal is via a data analyzer wherein the data analyzer comprises a component selected from the group consisting of: microprocessor; microcontroller; analog to digital converter; digital to analog converter; and combinations thereof.

170. The method of claim 148 wherein analyzing the verbal data signal comprises converting the verbal data signal to text data via spoken word recognition software employing at least one algorithm.

171. The method of claim 170 further comprising correlating at least a portion of the verbal data signal to one or more medical terms stored in a library.

172. The method of claim 148 wherein analyzing the verbal data signal comprises correlating at least a portion of the verbal data signal to one or more terms input by an operator.

173. The method of claim 148 wherein analyzing the verbal data signal comprises correlating at least a portion of the verbal data signal to at least one quantitative value or range of quantitative values input by an operator.

174. The method of claim 148 wherein analyzing the verbal data signal comprises correlating at least a portion of the verbal data signal to a range of quantitative values wherein the range comprises quantitative values that are typically associated with a parameter.

175. The method of claim 148 wherein analyzing the verbal data signal comprises correlating at least a portion of the verbal data signal to a previously received verbal data signal.

176. The method of claim 175 wherein the at least a portion of the verbal data signal comprises a quantitative value.

177. The method of claim 148 further comprising storing patient historic data.

178. The method of claim 177 wherein the stored patient data comprises data selected from the group consisting of: sex; age; height; weight; race; medical history; and combinations thereof.

179. The method of claim 177 further comprising extracting the patient historic data from the verbal data signal.

180. The method of claim 177 further comprising entering the patient historic data via an input device.

181. The method of claim 180 wherein the input device comprises a device selected from the group consisting of: a keyboard; a touch screen display; and combinations thereof.

182. The method of claim 148 further comprising identifying patient data in the verbal data signal.

183. The method of claim 182 wherein the patient data is selected from the group consisting of: ACT; blood pressure; heart rate; pulse rate; respiratory rate; glucose levels; saturated O2 pressure; saturated CO2 pressure; core body temperature; skin temperature; total lung capacity; residual volume; expiratory reserve volume; vital capacity; tidal volume; alveolar gas volume; actual lung volume; EEG bands comprising Delta, Theta, Alpha, Beta, Gamma and Mu; EKG information comprising RR interval, P wave length/amplitude, PR interval, amplitude of QRS complex, J-point detection, absolute and relative refractory periods, QT interval and U & J Wave detection; blood volume; extra embolic gases; heparin volume; protamine sulfate volume; and combinations thereof.

184. The method of claim 148 further comprising identifying equipment data in the verbal data signal.

185. The method of claim 184 wherein the equipment data is selected from the group consisting of: instructions to turn a piece of equipment on or off; instructions to modify at least one setting of one or more pieces of equipment; and combinations thereof.

186. The method of claim 148 further comprising identifying procedure data in the verbal data signal.

187. The method of claim 186 wherein the procedure data is selected from the group consisting of: total procedure length; length of a procedural step; time of initiation of a procedural step; time since last administration of a drug or other agent; and combinations thereof.

188. The method of claim 187 wherein the procedural steps are selected from the group consisting of: patient preparation; anesthesia induction; opening/sternotomy; initiation of bypass; cardiac repair; termination of bypass; closure; post-op; anesthesia; insufflation; laparoscopic insertion; diagnosis confirmation; port incisions; removing bile; grasping a structure; isolating and dividing structures; separation of a first structure from a second structure; removal of a structure; irrigation such as; prostatectomy; docking of a robot; dissection; hemostasis; completion of anastomosis; removal of drapes; and combinations thereof.

189. The method of claim 148 further comprising identifying a request for information data in the verbal data signal.

190. The method of claim 189 wherein the request for information data comprises a request for information selected from the group consisting of: a patient parameter; a procedural parameter; an equipment parameter; and combinations thereof.

191. The method of claim 189 further comprising providing a quantitative and/or qualitative response to the request.

192. The method of claim 148 further comprising identifying an acknowledgement of receipt of information wherein the identification of the acknowledgement is based on a library of acknowledgement terms.

193. The method of claim 148 further comprising correlating the verbal data signal to a first operator or to a second operator.

194. The method of claim 193 further comprising detecting the adverse condition via an algorithm, wherein the algorithm comprises a first analysis on data correlated to a first operator and a second, different analysis on data correlated to a second operator.

195. The method of claim 193 further comprising correlating the verbal data signal of the first operator based on a first identifier and correlating the verbal data signal of the second operator based on a second identifier, wherein the first identifier is different from the second identifier.

196. The method of claim 148 further comprising correlating the verbal data signal to an operator type.

197. The method of claim 196 further comprising detecting the adverse condition based on the operator type and the verbal data signal via an algorithm.

198. The method of claim 148 further comprising filtering and/or segregating verbal data received from at least one operator.

199. The method of claim 198 further comprising prioritizing the filtered and/or segregated verbal data based on an operator hierarchy.

200. The method of claim 148 further comprising filtering and/or segregating verbal data received from a non-operator.

201. The method of claim 148 further comprising storing data selected from the group consisting of: one or more portions of the verbal data signal; one or more processed data signals; a library of values where the values include spoken words to be recognized and/or quantitative values; historic medical statistics and/or other medical data; one or more portions of a video data signal produced by a video camera; and combinations thereof.

202. The method of claim 148 wherein the threshold comprises a value or a range of values input to the system by an operator.

203. The method of claim 148 wherein the threshold comprises a value or a range of values relating to at least one of a patient, procedural or equipment parameter.

204. The method of claim 148 wherein detecting the adverse condition is based on an identification of a key word in the verbal data signal.

205. The method of claim 148 wherein detecting the adverse condition is based on a detection of an unrecognized voice in the verbal data signal.

206. The method of claim 148 wherein detecting the adverse condition is based on a detection of an unrecognized term in the verbal data signal.

207. The method of claim 148 wherein detecting the adverse condition is based on a determination that a first operator has been active and/or present above a threshold of time.

208. A method for monitoring a medical procedure performed in a clinical environment comprising:
producing a verbal data signal representative of verbal communication that occurs in the clinical environment;
receiving the verbal data signal;
analyzing the verbal data signal;
detecting at least one adverse condition; and
alerting at least one operator when the at least one adverse condition is detected,
wherein detecting the adverse condition is based on a detection of a heightened frequency of recognized terms at an improper time.

209. The method of claim 148 wherein detecting the adverse condition is based on a lack of receipt of information.

210. The method of claim 148 wherein detecting the adverse condition is based on a determination that multiple pieces of similar data have not been received within a pre-determined time interval.

211. The method of claim 210 further comprising adjusting the time interval.

212. The method of claim 148 wherein detecting the adverse condition is based on a determination that a particular operator is not present.

213. The method of claim 148 wherein detecting the adverse condition is based on an analysis of patient historic data.

214. The method of claim 148 wherein detecting the adverse condition is based on an analysis of a set of medical statistics.

215. The method of claim 214 further comprising selecting the set of medical statistics.

216. The method of claim 148 wherein alerting the at least one operator when the adverse condition is detected comprises alerting a single operator.

217. The method of claim 148 wherein alerting the at least one operator when the adverse condition is detected comprises alerting multiple operators.

218. The method of claim 148 wherein alerting the at least one operator when the adverse condition is detected comprises producing at least one of an audible sound; a tactile feedback; or a visual display.

219. The method of claim 218 wherein detecting at least one adverse condition comprises detecting a first adverse condition and a second adverse condition, and wherein the method further comprises producing a first audio pattern when the first adverse condition is detected and a second audio pattern when the second adverse condition is detected.

220. The method of claim 148 further comprising entering data into a data input module.

221. The method of claim 220 wherein the data comprises voice data; text data; and combinations thereof.

222. The method of claim 220 wherein the data input module comprises a device selected from the group consisting of: a keyboard; a touch screen; a motion-sensing input device; a cell phone; a handheld electronic organizer; a mouse; a tablet; a hospital computer or computer network; a wireless connection; an internet connection; an electronic file transfer; a memory storage device; and combinations thereof.

223. The method of claim 220 wherein entering data comprises receiving operator voice data from a first operator via the input data module.

224. The method of claim 223 further comprising converting the verbal data signal to text data based on the received first operator voice data.

225. The method of claim 223 further comprising correlating the verbal data signal to the operator voice data to identify the first operator.

226. The method of claim 223 further comprising storing the operator voice data in a memory.

227. The method of claim 226 further comprising comparing the verbal data signal to the operator voice data stored in memory and converting the verbal data signal to text data.

228. The method of claim 223 further comprising storing quantitative data in memory.

229. The method of claim 228 further comprising comparing the verbal data signal to the quantitative data stored in the memory.

230. The method of claim 228 wherein the quantitative data stored in the memory comprises a threshold value used in the comparison.

231. The method of claim 220 further comprising transmitting information from a healthcare information system to the data input module.

232. The method of claim 148 further comprising providing patient and/or procedural information to at least one operator via an output module.

233. The method of claim 232 wherein the patient and/or procedural information provided in response to a request by the at least one operator.

234. The method of claim 232 wherein the patient and/or procedural information comprises information selected from the group consisting of: a current or real-time parameter; a historic parameter; an average of multiple parameter values; a maximum of multiple parameter values; and combinations thereof.

235. The method of claim 232 wherein providing the patient and/or procedural information comprises providing information in paper form.

236. The method of claim 232 wherein providing the patient and/or procedural information is providing information in electronic form.

237. The method of claim 232 wherein the patient and/or procedural information is selected from the group consisting of: an adverse condition detected; an operator's entry and/or exit time into the clinical setting; a procedure event that surpasses a threshold; an evidence-based decision support reminder; a captured video; a recommendation generated by the data analyzer; and combinations thereof.

238. The method of claim 232 further comprising transferring the patient and/or procedural information to and/or from a healthcare information system.

239. The method of claim 232 wherein providing the patient and/or procedural information occurs in real-time.

240. The method of claim 232 wherein providing the patient and/or procedural information occurs after completion of a procedure.

241. The method of claim 148 further comprising confirming proper information is received via a data monitoring module.

242. The method of claim 241 wherein confirming the proper information is received comprises confirming the proper information is continually received within a pre-determined time interval.

243. The method of claim 148 further comprising monitoring an operator position by detecting an operator voice in the verbal data signal via an operator position monitoring module.

244. The method of claim 243 wherein the operator position is monitored via at least one of a motion sensor; a video camera; or a timecard entry assembly.

245. The method of claim 148 further comprising sensing at least one parameter via at least one sensor.

246. The method of claim 245 wherein the at least one sensor comprises one or more sensors selected from the group consisting of: a temperature sensor; an acoustic sensor; an electromagnetic sensor; a pressure sensor; a motion sensor; and combinations thereof.

247. The method of claim 148 further comprising treating a patient via a patient treatment device.

248. The method of claim 247 wherein the treatment device is selected from the group consisting of: scalpel; electrocautery device; grasper; guidewire; interventional catheter; anesthesia injection device; RF or cryogenic ablation equipment; retractor; ECMO device; ventricular assist device; ventilator; bone awl; bone tamper; bone gouge; bone file; bone mallet; osteotome; defibrillator; drill; radiosurgery system; CPB machine; endoscope; cross clamp; robotic surgical system; colonoscope; polytectomy snare; and combinations thereof.

249. The method of claim 247 further comprising modifying the treatment device if an adverse event is detected.

250. The method of claim 249 wherein the modification comprises a disabling or powering down of the treatment device.

251. The method of claim 148 further comprising analyzing a checklist and detecting the at least one adverse condition based upon the analysis of the checklist.

252. The method of claim 251 further comprising customizing the checklist so that at least a portion of the checklist is customized for a particular operator.

253. The method of claim 252 wherein the checklist is customized prior to the performance of a medical procedure.

* * * * *